(12) United States Patent  
Agapie et al.

(10) Patent No.: US 7,847,099 B2  
(45) Date of Patent: Dec. 7, 2010

(54) NON-METALLOCENE ORGANOMETALLIC COMPLEXES AND RELATED METHODS AND SYSTEMS

(75) Inventors: Theodor Agapie, Berkeley, CA (US); Suzanne Rose Golisz, Pasadena, CA (US); Daniel Tofan, Pasadena, CA (US); John E. Bercaw, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 390 days.

(21) Appl. No.: 11/859,089

(22) Filed: Sep. 21, 2007

(65) Prior Publication Data

US 2008/0177020 A1    Jul. 24, 2008

Related U.S. Application Data

(60) Provisional application No. 60/846,385, filed on Sep. 21, 2006.

(51) Int. Cl.
```
C07F 7/00      (2006.01)
C07F 5/00      (2006.01)
B01J 31/00     (2006.01)
C08F 4/00      (2006.01)
```
(52) U.S. Cl. .............. 546/2; 549/3; 546/6; 534/15; 526/90; 526/348; 526/352; 502/103; 502/117

(58) Field of Classification Search ............. 502/103, 502/117; 526/90, 348, 352; 534/15; 546/2, 546/6; 549/3

See application file for complete search history.

(56) References Cited

U.S. PATENT DOCUMENTS

| | | | |
|---|---|---|---|
| 6,998,363 B2 | 2/2006 | Chan et al. | |
| 7,105,672 B2 | 9/2006 | Chan et al. | |
| 7,164,020 B2 | 1/2007 | Vogel | |
| 2007/0249798 A1 | 10/2007 | Stevens et al. | |
| 2010/0022726 A1 | 1/2010 | Hagadorn et al. | |

OTHER PUBLICATIONS

PCT International Search Report for PCT/US2007/079137 filed on Sep. 21, 2007in the name of California Institute of Technology et al.

Britovsek, G. J. P. et al. "The Search for New-Generation Olefin Polymerization Catalysts: Life beyond Metallocenes" in *Angew. Chem., Int. Ed. Engl.* (1999) 38, 428-447.

Burger, B.J.; Bercaw, J.E. Vacuum Line Techniques for Handing Air-Sensitive Organometallic Compounds. In "New Developments in the Synthesis, Manipulation and Characterization of Organometallic Compounds" Wayda, A.L.; Darensbourg, M.Y., Eds.; ACS Symposium Series 357; American Chemical Society: Washington, D.C., 1987; pp. 79-98.

(Continued)

*Primary Examiner*—Porfirio Nazario Gonzalez  
(74) *Attorney, Agent, or Firm*—Steinfl & Bruno

(57) ABSTRACT

A non-metallocene organometallic complex comprising a tridentate ligand and a metal bonded to a tridentate ligand, wherein two substituted aryl groups in the tridentate ligand are connected to a cyclic group at the ortho position via semi-rigid ring-ring linkages, and selected so to provide the resulting non-metallocene organometallic complex with a $C_S$ geometry, a $C_1$ geometry, a $C_2$ geometry or a $C_{2v}$ geometry. Method for performing olefin polymerization with a non-metallocene organometallic complex as a catalyst, related catalytic systems, tridentate ligand and method for providing a non-metallocene organometallic complex.

30 Claims, 14 Drawing Sheets

OTHER PUBLICATIONS

Chan, Michael C. W. "Surprising activity for Group 4 polyolefin catalysts [M{(OAr)2py}Cl2(thf )] (M _ Zr, Ti) bearing tridentate pyridine-2,6-bis(aryloxide) ligands" in *J. Chem. Soc., Dalton Trans.* (2002) p. 3085-3087.

Chan, Michael C. W. et al. "Synthesis, Structures, and Olefin Polymerization Characteristics of Group 4 Catalysts [Zr{OAr)2py}Cl2(D)] (D ) O-Donors, Cl[HPR3] Supported by Tridentate Pyridine-2,6-bis(aryloxide) Ligands S." in *Organometallics* (2006) 25, p. 785-792.

Coates, G. W. "Precise Control of Polyolefin Stereochemistry Using Single-Site Metal Catalysts" in *Chem. Rev.* (2000) 100, p. 1223-1252.

Coates, G.W. et al. "Oscillating Sterocontrol: A Strategy for the Synthesis of Thermoplastic Elastomeric Polypropylene" in *Science*, vol. 267, No. 5195 (Jan. 1995) p. 217-219.

Coates, G. W. et al. "Catalysts for the Living Insertion Polymerization of Alkenes" in *Angew. Chem., Int. Ed. Engl.* (2002) 41, p. 2236-2257.

Evans, D.F. "The Determination of the Paramagnetic Susceptibility of Substances in Solution by Nuclear Magnetic Resonance" in *J. Chem. Soc.* (1959) p. 2003-2005.

Froese, R. D. J. et al. "Theoretical Studies of the Factors Controlling Insertion Barriers for Olefin Polymerization by the Titanium-Chelating Bridged Catalysts. A Search for More Active New Catalysts" in *Organometallics* (1999), 18, p. 373-379.

Ittel, Steven D. et al. "Late-Metal for Ethylene Homo- and Copolymerization" in *Chem. Rev.* (2000) 100, p. 1169-1203.

Gademann, Karl, "Highly Enantioselective Inverse-Electron-Demand Hetero-Diels-Alder Reactions of α,β-Unsaturated Aldehydes" in *Angew. Chem. Int. Ed.* (2002) 41, p. 3059-3061.

Gibson, V. C. et al. "Advances in Non-Metallocene Olefin Polymerization Catalysis" in *Chem. Rev.* (2003) 103, p. 283-315.

Guerin, F. et al. "Conformationally Rigid Diamide Complexes of Zirconium: Electron Deficient Analogues of Cp2Zr" in *Organometallics* (1996) 15, p. 5586-5590.

Gauvin. R. et al. Zirconium-Benzyl Complexes of a Tridentate C2-Symmetric Dialkoxo Ligand. Diastereoselectivity of Olefin Single-Insertion Reactions in *Organometallics* (2000) 19, p. 2944-2946.

Li, Y. et al. "A Mixed Pyridine—phenol Boron Complex as an Organic Electroluminescent Material" in *Chem. Commun.* (2000) p. 1551-1552.

Mack, H. et al. "A pyridine dialkoxide titanium dichloride complex. Synthesis and molecular structure of 2,6-bis(2,2-diphenyl-2-trimethylsilyloxyethyl) pyridine" in *J. Chem. Soc., Dalton Trans.* (1998) p. 917-921.

Marvich. R.H. et al "A Metastable Form of Titanocene. Formation from a Hydride Complex and Reactions with Hydrogen, Nitrogen, and Carbon Monoxide" in *J. Am. Chem. Soc.* (1971) 93, p. 2046.

Mason, A. F. et al "New Phenoxyketimine Titanium Complexes: Combining Isotacticity and Living Behavior in Propylene Polymerization" in *J. Am. Chem. Soc.* (2004) 126, p. 16326-16327.

Manzer, L.E. "Tetrahydrofuran Complexes of Selected Early Transition Metals" in *Inorg. Syn.* (1982) 21, p. 135-140.

Mehrkhodavandi, P. et al. "Living Polymerization of 1-Hexene by Cationic Zirconium and Hafnium Complexes that Contain a Diamido/Donor Ligand of the Type [H3CC(2-C5H4N)(CH2NMesityl)2]2-. A Comparison of Methyl and Isobutyl Initiators" in *Organometallics* (2003) 22, p. 4569-4583.

Milano, Giuseppe et al "Site Chirality as a Messenger in Chain End Stereocontrolled Propene Polymerization" in *J. Am Chem Soc.* (2002) 124, p. 13368-13369.

Mitani, M et al. Syndiospecific Living Propylene Polymerization Catalyzed by Titanium Complexes Having Fluorine-Containing Phenoxy-Imine Chelate Ligands in T. *J. Am. Chem. Soc.* (2003) 125, p. 4293-4305.

Nakayama, Y. et al. Titanium Complexes Having Chelating Diaryloxo Ligands Bridged by Tellurium and Their Catalytic Behavior in the Polymerization of Ethylene in *Organometallics* (2000) 19, p. 2498-2503.

Pangborn, A. B. et al. "Safe and Convenient Procedure for Solvent Purification" in *Organometallics* (1996) 15, p. 1518-20

Pellecchia, Claudio et al. "Non-metallocene group 4 organometallic complexes as catalysts for olefin polymerization: synthesis and catalytic activity . . . " in *J. Molecular Catalysis*, 82 (1993) p. 57-65.

Resconi, L. et al "Selectivity in Propene Polymerization with Metallocene Catalysts" in *Chem. Rev.* (2000) 100, p. 1253-1345.

Segal, Sharon et al. "Zirconium and Titanium Diamine Bis(phenolate)Catalysts for r-Olefin Polymerization: From Atactic Oligo(1-hexene) to Ultrahigh-Molecular-Weight Isotactic Poly(1-hexene)" in *Organometallics* (2005) 24, p. 200-202.

Steinhauser, S. et al. "Complex Formation of 2,6-Bis-(2_-hydroxyphenyl)pyridine with AlIII, FeIII and CuII" in *Anorg. Allg. Chem.* (2004) 630, p. 1829-1838.

Takaoki, Kazuo, et al. "Titanium and Vanadium based non-metallocene catalysts for Olefin Polymerization" in Macromol.Symp. 157, p. 251-257 (2000).

Tian, Jun et al "A New Catalyst for Highly Syndiospecific Living Olefin Polymeriization:" in *J. Am. Chem* (2001) 123, p. 5134-5135.

Zucchini, U. et al. "Benzylzirconium Compounds" in *J. Chem. Soc. Chem. Comm.* (1969) 20, p. 1174-1175.

Written Opinion for PCT/US2007/079137 filed on Sep. 21, 2007 in the name of California Institute of Technology.

Arriola, D., et al., Catalytic Production of Olefin Block Copolymers via Chain Shuttling Polymerization, Science 2006, 312:714-719.

Kui, S., et al., Observation of Intramolecular C_H•••F_C Contacts in Non-Metallocene Polyolefin Catalysts:Model forWeak Attractive Interactions between Polymer Chain and Noninnocent, Angew. Chem. Int. Ed. 2003, 42: 1628-1632.

Chan. M., Synthetic Models of Weak Attractive Ligand-Polymer Interactions in Olefin Polymerization Catalysts, Macromolecular Chemistry and Physics 2007, 208: 1845-1852.

Chan, M., et al., Neutron and X-ray Diffraction and Spectroscopic Investigations of Intramolecular [C_H•••F_C] Contacts in Post-Metallocene Polyolefin Catalysts: Modeling Weak Attractive Polymer—Ligand Interactions, Chem. Eur. J. 2006, 12: 2607-2619.

Chan, M., et al., Surprising activity for Group 4 polyolefin catalysts [M{(OAr)2py}Cl2(thf )] (M_Zr, Ti) bearing tridentate pyridine-2,6-bis(aryloxide) ligands, J. Chem. Soc. 2002, 3085-3087.

Boussie, T., et al., Nonconventional Catalysts for Isotactic Propene Polymerization in Solution Developed by Using High-Throughput-Screening Technologies, Angew. Chem. Int. Ed. 2006, 2006: 3278-3283.

Chan, M., et al., Synthesis, Structures, and Olefin Polymerization Characteristics of Group 4 Catalysts [Zr{(OAr)2py}Cl2(D)] (D ) O-Donors, Cl[HPR3]) Supported by Tridentate Pyridine-2,6-bis(aryloxide) Ligands, Organometallics 2006, 25: 785-792.

Tam, K., et al., Cyclometalated group 4 complexes supported by tridentatepyridine-2-phenolate-6-(r-aryl) ligands: Catalysts for ethylene polymerization and comparisons with fluorinated analogues, Journal of Organometallic Chemistry 2007, 692: 4750-4759.

Tam, K., et al., Indirect Substituent Effects upon the Olefin Polymerization Reactivity of Titanium(Iv) Chelating σ-Aryl Catalysts, Organometallics 2009, 28: 5877-5882.

Scheme 2

Scheme 3

Scheme 4

NON-METALLOCENE ORGANOMETALLIC COMPLEXES AND RELATED METHODS AND SYSTEMS

CROSS REFERENCE TO RELATED APPLICATIONS

This application claims priority to U.S. Provisional Application Ser. No. 60/846,385 filed on Sep. 21, 2006, the content of which is incorporated herein by reference in its entirety.

STATEMENT OF GOVERNMENT GRANT

The U.S. Government has certain rights in this invention pursuant to Grant No. DE-FG03-85ER13431/S-113,044 awarded by the Department of Energy.

TECHNICAL FIELD

The present disclosure relates to the field of olefin polymerization, and in particular pertains to non-metallocene organometallic complexes suitable as catalysts in the preparation of olefin polymers.

BACKGROUND

The last half-a-century has seen great developments in olefin polymerization catalysis and particularly in the ability to modify polymer architecture and physical properties by controlling the structure of the catalyst. Design of well-defined, single-site catalysts has emerged as a powerful method to control polymer features such as tacticity, molecular weight, molecular weight distribution, and amount of comonomer incorporation.

Early transition metal metallocene complexes have provided the most important and well-studied framework for single-site catalysts for olefin polymerization. (Coates, G. W. *Chem. Rev.* 2000, 100, 1223-1252. Resconi, L.; Cavallo, L.; Fait, A.; Piemontesi, F. *Chem. Rev.* 2000, 100, 1253-1345.) Recently, non-metallocene frameworks have emerged as versatile alternatives. (Gibson, V. C.; Spitzmesser, S. K. *Chem. Rev.* 2003, 103, 283-315. Britovsek, G. J. P.; Gibson, V. C.; Wass, D. F. *Angew. Chem., Int. Ed. Engl.* 1999, 38, 428-447. Coates, G. W.; Hustad, P. D.; Reinartz, S. *Angew. Chem., Int. Ed. Engl.* 2002, 41, 2236-2257.) Complexes based on iron, cobalt, nickel and palladium have been shown to polymerize and oligomerize olefins with good activities and sometimes in a living fashion. (Ittel, S. D.; Johnson, L. K.; Brookhart, M. *Chem. Rev.* 2000, 100, 1169-1203.)

In the realm of early transition metal polymerization catalysis, frameworks displaying an extensive range of multidentate ligands have been utilized. In this context, a broad interest has been shown in generating polymers with controlled microstructure through the use of non-metallocene catalysts. Promising advances have been made in both the development of single-site living polymerization catalysts and the design of ancillary ligands that have the appropriate symmetry for polymer tacticity control. The fundamental polymerization behaviors observed for individual systems are not yet well understood. Thus further exploration into the field of non-metallocene olefin polymerization catalysis is required. These frameworks also present the advantage of being relatively inexpensive and easy to both prepare and modify.

Anilides and phenolates are common anionic donors found in multidentate ligands for polymerization catalysis. Some of the most successful non-metallocene polymerization catalysts include bi-, tri-, and tetradentate anilide and phenolate ligands. Tridentate bisanilide ligands have been reported to support ethylene and α-olefin polymerization; in some cases living polymerization of 1-hexene was possible. (Mehrkhodavandi, P.; Schrock, R. R.; Pryor, L. L. *Organometallics* 2003, 22, 4569-4583.) Bidentate imino-phenolate ligands have been shown to support $C_2$-symmetric architectures; these catalysts are able to generate syndiotactic or isotactic polypropylene depending on the nature of the substituents on the phenolate rings. (Mason, A. F.; Coates, G. W. *J. Am. Chem. Soc.* 2004, 126, 16326-16327. Mitani, M.; Furuyama, R.; Mohri, J.; Saito, J.; Ishii, S.; Terao, H.; Nakano, T.; Tanaka, H.; Fujita, T. *J. Am. Chem. Soc.* 2003, 125, 4293-4305.)

Tetradentate bisphenolate frameworks have been reported to give very active catalysts for the polymerization of 1-hexene; again, tacticity control was possible by use of $C_2$-symmetric architectures. (Segal, S.; Goldberg, I.; Kol, M. *Organometallics* 2005, 24, 200-202.)

Tridentate bisphenolate frameworks have been successful as well in supporting olefin polymerization. (Takaoki, K.; Miyatake, T. *Macromol. Symp.* 2000, 157, 251-257. Nakayama, Y; Watanabe, K.; Ueyama, N.; Nakamura, A.; Harada, A.; Okuda, J. *Organometallics* 2000, 19, 2498-2503.)

With respect to olefin polymerization activity, a number of related systems have been investigated, based on the pyridine linker with phenoxides, alkoxides, or anilides as the anionic donors. (Chan, M. C. W.; Tam, K. H.; Pui, Y. L.; Zhu, N. Y. *J. Chem. Soc., Dalton Trans.* 2002, 3085-3087. Chan, M. C. W.; Tam, K. H.; Zhu, N. Y.; Chiu, P.; Matsui, S. *Organometallics* 2006, 25, 785-792. Mack, H.; Eisen, M. S. *J. Chem. Soc., Dalton Trans.* 1998, 917-921. Guerin, F.; McConville, D. H.; Vittal, J. J. *Organometallics* 1996, 15, 5586-5590. Gauvin, R. M.; Osborn, J. A.; Kress, J. *Organometallics* 2000, 19, 2944-2946.) It was found that a zirconium pyridine bisphenoxide system can polymerize ethylene with high activities and also incorporate propylene.

In this connection, a ligand involving a pyridine linker and two phenoxides was reported by to bind to iron(III), copper (II), and aluminum(III) in a $C_2$ fashion. (Steinhauser, S.; Heinz, U.; Sander, J.; Hegetschweiler, K. *Z. Anorg. Allg. Chem.* 2004, 630, 1829-1838.) When bound to boron (Li, Y. Q.; Liu, Y; Bu, W. M.; Guo, J. H.; Wang, Y. *Chem. Commun.* 2000, 1551-1552.) or zirconium(IV) this ligand binds in a $C_s$ fashion.

A chiral cationic zirconium pyridine bisalkoxide was found to insert only one ethylene molecule, (Gauvin, R. M.; Osborn, J. A.; Kress, J. *Organometallics* 2000, 19, 2944-2946.) while a related titanium pyridine bisalkoxide was reported to polymerize ethylene with good activity. (Mack, H.; Eisen, M. S. *J. Chem. Soc., Dalton Trans.* 1998, 917-921.) A zirconium pyridine bisanilide system was shown to polymerize ethylene upon activation with MAO. (Guerin, F.; McConville, D. H.; Vittal, J. J. *Organometallics* 1996, 15, 5586-5590.) Notably, computational studies on bisphenoxide-donor systems indicated that a strong interaction with the additional donor lowers the transition state for olefin insertion. (Froese, R. D. J.; Musaev, D. G.; Morokuma, K. *Organometallics* 1999, 18, 373-379.)

SUMMARY

Provided herein are non-metallocene organometallic complexes suitable as olefin polymerization catalysts and related methods and systems. In particular, provided herein are non-metallocene organometallic complexes that are designed to have geometries related to known metallocene systems used for olefin polymerization. In particular, in the non-metallocene organometallic complexes herein described aryl groups are included that are designed to have geometries sterically related to known appropriately substituted metallocene systems suitable for olefin polymerization.

According to a first aspect a non-metallocene organometallic complex is disclosed, the non-metallocene organometallic complex comprising tridentate ligand and a metal bonded to a tridentate ligand. In the non-metallocene organometallic complex, the tridentate ligand comprises a first substituted aryl group, a second substituted aryl group and a cyclic group, each of the first and second substituted aryl groups substituted with at least an anionic donor, each of the first and second substituted aryl group connected to the cyclic group via semi-rigid ring-ring linkages at the ortho position with respect to the anionic donor, wherein the metal, the first substituted aryl group, the second substituted aryl group, and the cyclic group are selected to provide the resulting non-metallocene organometallic complex with a $C_s$ geometry, a $C_1$ geometry, a $C_2$ geometry or a $C_{2v}$ geometry.

According to a second aspect a method for polymerizing olefins is described, the method comprising contacting an olefin with an organometallic complex herein described. In some embodiments contacting an olefin with an organometallic complex herein described is performed in a reaction mixture further comprising a suitable activator.

According to a third aspect, a catalytic system for olefin polymerization is described, the system comprising a non-metallocene organometallic complex of herein described and a suitable activator.

According to a fourth aspect, A process for preparation of a non-metallocene organometallic complex is described, the process comprising: selecting a metal, a first substituted aryl group, a second substituted aryl group and a cyclic group to provide the resulting non-metallocene organometallic complex with a $C_s$ geometry, a $C_1$ geometry, a $C_2$ geometry or a $C_{2v}$ geometry. The process further comprises, contacting the selected first substituted aryl group, second substituted aryl group and a cyclic group to provide a tridentate ligand, the tridentate ligand comprising a first substituted aryl group, a second substituted aryl group and a cyclic group, each of the first and second substituted aryl groups substituted with at least an anionic donor, each of the first and second substituted aryl group connected to the cyclic group via semi-rigid ring-ring linkages at the ortho position with respect to the anionic group, The process also comprises contacting the tridentate ligand with a metal to provide a non-metallocene organometallic complex, thus obtaining a non-metallocene organometallic complex with a $C_s$ geometry, a $C_1$ geometry, a $C_2$ geometry or a $C_{2v}$ geometry.

According to a fifth aspect a tridentate ligand is described, the tridentate ligand comprising a first substituted aryl group, a second substituted aryl group and a cyclic group. In the tridentate ligand each of the first and second substituted aryl groups substituted with at least an anionic donor, each of the first and second substituted aryl group connected to the cyclic group via semi-rigid ring-ring linkages at the ortho position with respect to the anionic group. In the tridentate ligand the first substituted aryl group and the second substituted aryl group are selected so that when bonded to a metal in a non-metallocene organometallic complex comprising the tridentate ligand with a $C_s$ geometry, a $C_1$ geometry, a $C_2$ geometry or a $C_{2v}$ geometry.

A first advantage of the organometallic complexes methods and systems herein described is that organometallic complexes herein provided can be used in place of metallocene organometallic complexes in applications wherein metallocene organometallic complexes are usually employed and in particular for production of polyolefins and in particular poly($\alpha$-olefins), with associated advantages in terms of costs and ease of use.

A second advantage of the organometallic complexes methods and systems herein described is that the non-metallocene organometallic complexes herein provided can be used to generate polyolefins (and in particular poly($\alpha$-olefins)) having a predetermined tacticity, wherein the geometry of the organometallic complex determines the polymer tacticity, so that atactic, isotactic or syndiotactic polymers can be produced. In particular stereoblock copolymers may also be produced by a non-metallocene organometallic complex that can have wherein different geometries wherein the equilibrium between different geometries is controlled.

A third advantage of the of the organometallic complexes methods and systems herein described is the ability of organometallic complexes herein provided to produce polyolefins and in particular poly($\alpha$-olefins) having a molecular weight within a predetermined molecular weight range. In particular, by choosing an appropriate metal/ligand combination the molecular weight range of polyolefins produced by reactions catalyzed by the organometallic complexes herein described can be controlled. Additionally, the molecular weight range can be controlled by careful consideration of the amount and type of activator or chain transfer agent.

A fourth advantage of the organometallic complexes methods and systems herein described is that enantiopure non-metallocene organometallic complexes herein described, such as $C_1$- and $C_2$-enantiopure non-metallocene organometallic complexes can be used in enantioselective transformations such as kinetic resolution of racemic $\alpha$-olefins, alkylation of carbonyl compounds, epoxidations, and other transformations identifiable by the skilled person upon reading of the present disclosure.

A fifth advantage of the non-metallocene organometallic complexes methods and systems herein described is that non-metallocene organometallic complexes herein described can be used to provide polymers via organometallic transformations such as C—H bond activation to provide a cyclometallated product, in the absence of activators.

Non-metallocene organometallic complexes are herein also provided, that can be used as a Lewis acid in reactions wherein inclusion of a Lewis acid in the reaction mixture is required or in any case desired. Accordingly, in a sixth aspect of the present invention, a method to perform a reaction is disclosed, the method comprising providing a reaction mixture including a Lewis acid, wherein the Lewis acid is a non-metallocene organometallic complex herein described.

An advantage of using the non-metallocene organometallic complexes described herein as Lewis acids is their relative ease of preparation and inexpensiveness, as well as the possibility to use enantiopure versions.

The details of one or more embodiments of the invention are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description, serve to explain the principles and implementations of the complexes, systems and methods herein disclosed.

In the drawings.

Like reference symbols in the various drawings indicate like elements.

DETAILED DESCRIPTION

Figure 1:
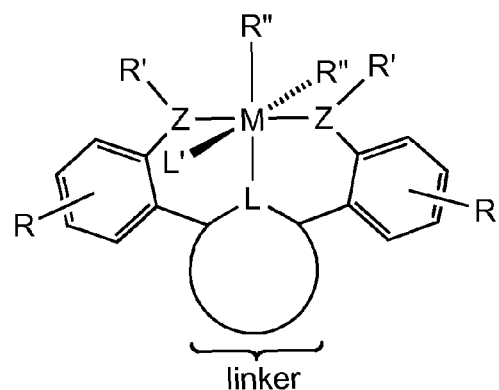
FIG. 1 shows a schematic illustration of a general structure of a non-metallocene organometallic complex according to an embodiment herein described.

Non-metallocene organometallic complexes are herein described, which comprise a tridentate ligand including a first and second of substituted aryl groups (e.g. bisphenolates and bisanilides) each substituted with at least one anionic donor and, connected to a cyclic group such as a heterocycle, aryl, or other cyclic group, via semi-rigid, ring-ring linkages at the at the ortho position with respect to the anionic donor. In the non-metallocene organometallic complexes the first and second substituted aryl group can have the same or different chemical structure. This configuration allows production of non-metallocene organometallic complexes having a geometry typical of metallocene organometallic complexes by proper selection of metal, first substituted aryl group, second substituted aryl group and cyclic group.

In particular, in embodiments wherein the metal is a second or third row transition metal and the nature and dimensions of the first and second substituted aryl group and cyclic group do not significantly affect the symmetry of the organometallic complex, a non-metallocene organometallic complex having a $C_s$ geometry can be provided.

In embodiments, wherein the first and second substituted aryl groups and/or the cyclic group are unsymmetrical, a non-metallocene organometallic complex having a $C_1$ or $C_S$ geometry can be provided.

In embodiments, wherein the first and second substituted aryl groups are symmetrical and one of the semi-rigid ring-ring linkage rotate in either direction with the cyclic group not significantly affecting the symmetry of the non-metallocene organometallic complexes, a non-metallocene organometallic complex having a $C_1$ geometry can be provided In embodiments, wherein the metal is a first row transition metal and the first and second substituted aryl groups or the anionic donor can be substituted with a bulky, i.e. sterically encumbered substituent, such as a group that has a size larger than a t-butyl group, while the nature and dimensions of the cyclic group does not significantly affect the symmetry of the non-metallocene organometallic complex, a non-metallocene organometallic complex having a $C_2$ geometry can be provided In embodiments, wherein the tridentate ligand is symmetrical and the first and second substituted aryl group and/or the anionic donor are substituted with a small, i.e. sterically unencumbered substituent such as a group that is smaller in size than a t-butyl group, a non-metallocene organometallic complex having a $C_{2v}$ geometry can be provided Chemical properties and in particular catalytic activities, associated to each of the $C_1$ $C_{2v}$ $C_2$ and $C_s$ geometries related to metallocene organometallic complexes are known or identifiable by a skilled person upon reading of the present disclosure and include determination of the stereoisometry of a reaction product, determination of the molecular weight of a reaction product and determination of the chirality of a reaction product, in reactions, such as polymerization of olefins and in particular of α-olefins.

In particular, within the field of metallocene catalyzed olefin polymerization, a well-documented and predictable relationship between complex symmetry and polymer tacticity has emerged. More in particular, complexes with $C_{2v}$-symmetry give atactic polymer as do $C_S$-symmetric complexes when the mirror plane is perpendicular to the page (FIG. 2c). Conversely, $C_S$-symmetric complexes with the mirror plane in the plane of the paper (FIG. 2e) generate syndiotactic polymers. $C_2$-symmetric complexes produce isotactic polymer. $C_1$-symmetric complexes are relatively unpredictable, yet they usually generate isotactic, atactic or an isotactic-atactic stereoblock copolymer. Additional features and properties of the metallocene counterparts are described in the art (for catalyst structure and polymer produced see for example Coates, G. W. "Precise Control of Polyolefin Stereochemistry Using Single-Site Metal Catalysts." Chemical Reviews, 2000, 100 (4), 1223-1252 incorporated herein by reference in its entirety) and/or identifiable by the skilled person upon reading of the present disclosure and therefore will not be further herein described in detail.

Figure 2:
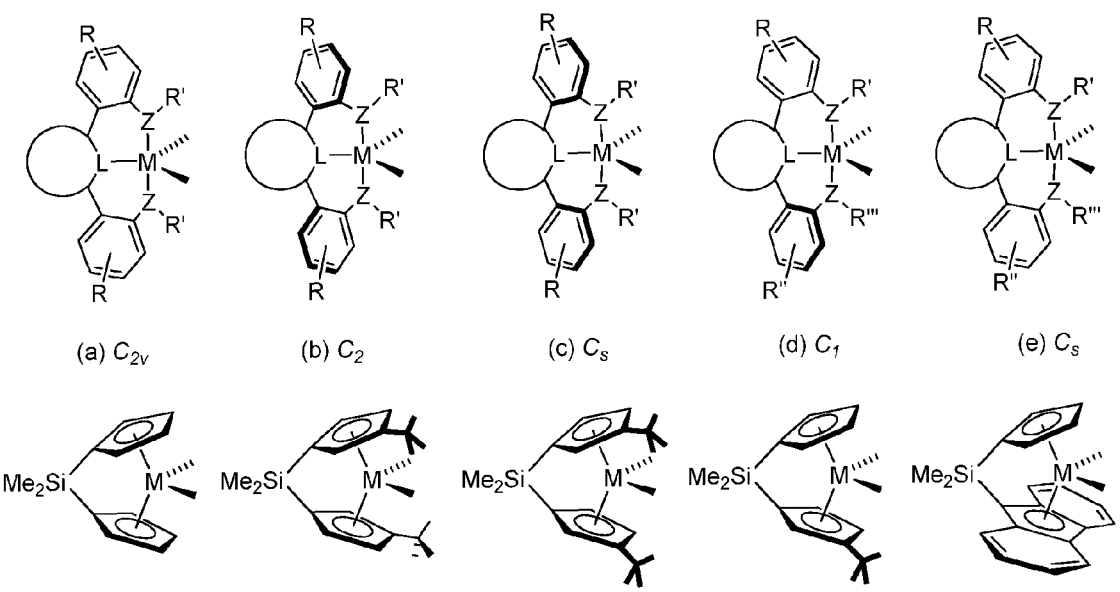
FIG. 2. shows a schematic illustration of possible geometries of the semi-rigid ligand framework of organometallic complexes according to an embodiment herein described with their relation to metallocene complexes.

Exemplary metallocene geometries of non-metallocene organometallic complexes used for the polymerization of olefins, are illustrated in FIG. 2, for the exemplary organometallic complexes illustrated in FIG. 1

In particular, in the illustration of FIG. 2, $C_{2v}$, $C_2$ and $C_s$ geometries for the exemplary non-metallocene organometallic complexes of FIG. 1 are shown wherein each geometry is associated with a substitution pattern of the substituted aryl group (e.g. phenolate or anilide rings) and the binding geometry of the ligand, as discussed above and further illustrated in the following disclosure.

In some embodiments, the cyclic group, or linker, is selected between a neutral or an anionic cyclic group to provide a dianionic or trianionic ligand in the non-metallocene organometallic complexes herein disclosed, wherein dianionic and trianionic ligands affect the catalytic activity of the resulting non-metallocene organometallic complexes as further illustrated below.

In some embodiments, the cyclic group is selected between a 5 and 6 membered cyclic group, wherein the size and dimension of the cyclic group affect the molecular weight of the product, as further illustrated below.

In some embodiments the configuration of the tridentate ligand is such that a binding pocket for the metal is formed, the binding pocket having a size depending on nature and substitution of the first and second substituted aryl group and cyclic group, wherein the interaction between the metal and the pocket determines the symmetry of the resulting non-metallocene organometallic complex.

In some embodiments the tridentate ligand is a has the structure of formula

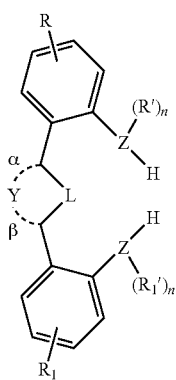

(I)

wherein

L is an atom that when contacted with a metal can donate one or more of its electrons through a coordinate covalent bond to, or shares its electrons through a covalent bond with the metal Z is a group 14, a group 15 or group 16 anionic donor, Y is a an organic fragment selected from the group consisting of a hydrocarbylene, substituted hydrocarbylene, heteroatom-containing hydrocarbylene or substituted heteroatom-containing hydrocarbylene linker, wherein Y and L are linked together to form a cyclic group;

R, $R_1$, R' and $R'_1$ are independently selected from hydrogen, hydrocarbyl, substituted hydrocarbyl, heteroatom containing hydrocarbyl, or other functional group;

α and β are independently single or multiple bonds.

n is 0, 1 or 2, and in particular when Z is a group 14 anionic donor n is 2, when Z is a group 15 anionic donor n=1 and when Z is a group 16 anionic donor n=0, and The semi-rigid tridentate ligand of formula (I) can exhibit a variety of different geometries depending on the identity of L, Y, and R, and in particular on the size and nature of L Y and the related cyclic group. In some embodiments, the cyclic group, and the substituted aryl groups are on the same plane (e.g. when the cyclic group is a pyridine). In other embodiments, the linkage Y will be out of the plane formed by at least one of the substituted aryl groups (e.g. when the cyclic group is thiophene, furan, and phenyl). Additionally, the non-linker rings (the substituted aryl group) are not required to be in the same plane with each other. These geometries may or may not be retained once bound to a metal in an organometallic complex.

In some embodiment, Y and L are linked together to form a 5-membered cyclic group such as furan or thiophene.

In some embodiment, Y and L are linked together to form a 6-membered cyclic group such as phenyl or pyridine.

In some embodiments L is an X-type donor and the resulting tridentate ligand is trianionic tridentate ligand.

In some embodiments L is an L-type donor and the resulting tridentate ligand is dianionic tridentate ligand.

In some embodiments R and $R_1$ have same chemical structure.

In some embodiments the ligand of formula (I) is bonded to a metal to form the non-metallocene organometallic complex has the structure of formula (II)

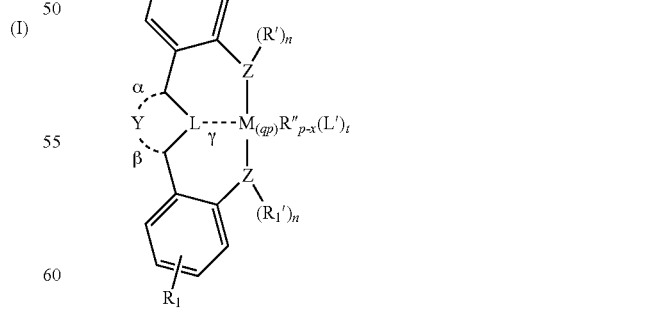

(II)

wherein

M is a metal, q is the metal coordination number and is 4, 5 6, or 7, p is the metal oxidation state and is any state from 0 to +6, and x is 2 or 3;

L' is a neutral coordinating group, displaying a group 15 or 16 atom donor,

Z is a group 14, a group 15 or group 16 anionic donor,

L is an atom that can donate one or more of its electrons through a coordinate covalent bond to, or shares its electrons through a covalent bond with the metal Y is an organic fragment, selected from the group consisting of a hydrocarbylene, substituted hydrocarbylene, heteroatom-containing hydrocarbylene or substituted heteroatom-containing hydrocarbylene linker, wherein Y and L are linked together to form a cyclic group, α, β and γ are independently single or multiple bonds;

R, $R_1$, R', $R'_1$ and R" are independently selected from hydrogen, hydrocarbyl, substituted hydrocarbyl, heteroatom containing hydrocarbyl, and functional groups, and might be the same or different;

n is 0, 1 or 2, and in particular when Z is a group 14 anionic donor n is 2, when Z is a group 15 anionic donor n=1 and when Z is a group 16 anionic donor n=0, and t is 0, 1, 2 or 3

$$t=q-3-(p-x) \text{ and}$$

$$q \geq p$$

In particular, in the non-metallocene organometallic complexes of formula (II) when x is 2 the tridentate ligand is trianionic, and when x is 3 the tridentate ligand is trianionic.

The wording "having the structure of formula" or "having the formula" is not intended to be limiting and is used in the same way that the term "comprising" is commonly used.

The wording "anionic donor" as used herein identifies a group having formal negative charge which binds to the metal center, including but not limited to a halide or alkyl groups.

The term "ligand" as used herein identifies an atom or a group that coordinates to a metal center which may or may not have formal charge, as both halides and solvent molecules are members of this definition, and may or may not have multiple donor atoms.

The wording "neutral coordinating group" as used herein indicates a donor that does not have a formal charge which binds to the metal center such as a solvent molecule.

The term "hydrocarbylene" refers to divalent groups formed by removing two hydrogen atoms from a hydrocarbon, the free valencies of which may or may not be engaged in a double bond, typically but not necessarily containing 1 to 20 carbon atoms, preferably 1 to 12 carbon atoms and more preferably 1 to 6 carbon atoms which includes but is not limited to linear cyclic, branched, saturated and unsaturated species, such as alkylene, alkenylene alkynylene and divalent aryl groups e.g. 1,3-phenylene, —$CH_2CH_2CH_2$— propane-1,3-diyl, —$CH_2$— methylene, —CH=CH—CH=CH—. The term "hydrocarbyl" as used herein refers to univalent groups formed by removing a hydrogen atom from a hydrocarbon, typically but not necessarily containing 1 to 20 carbon atoms, preferably 1 to 12 carbon atoms and more preferably 1 to 6 carbon atoms, including but not limited to linear cyclic, branched, saturated and unsaturated species, such as univalent alkyl, alkenyl, alkynyl and aryl groups e.g. ethyl and phenyl groups.

The term "alkyl" as used herein refers to a linear, branched, or cyclic saturated hydrocarbon group (from which a terminal hydrogen atom was removed) typically although not necessarily containing 1 to about 20 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. The term "lower alkyl" intends an alkyl group of 1 to 6 carbon atoms, and the specific term "cycloalkyl" intends a cyclic alkyl group, typically having 4 to 8, preferably 5 to 7, carbon atoms. If not otherwise indicated, the terms "alkyl" and "lower alkyl" include linear, branched, cyclic, unsubstituted, substituted, and/or heteroatom-containing alkyl, and lower alkyl, respectively. Where the substituents can be "aryl" or "heteroatom-containing aryl" such as benzyl.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above. The term "alkynyl" as used herein refers to a linear or branched hydrocarbon group of 2 to about 20 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. If not otherwise indicated, the terms "alkynyl" and "lower alkynyl" include linear, branched, unsubstituted, substituted, and/or heteroatom-containing alkynyl and lower alkynyl, respectively.

The term "alkynylene" as used herein refers to a difunctional alkynyl group, where "alkynyl" is as defined above.

The term "aryl," as used herein and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like.

The wording "substituted hydrocarbyl," "substituted alkyl," "substituted alkenyl", "substituted alkynyl", "substituted aryl" respectively refers to hydrocarbyl, alkyl, alkenyl, alkynyl and aryl groups substituted with one or more substituent groups, and the terms "heteroatom-containing hydrocarbyl," "heterohydrocarbyl," "heteroatom-containing alkyl," "heteroatom-containing alkenyl," "heteroatom-containing alkynyl," "heteroatom-containing aryl" refer to hydrocarbyl, alkyl, alkenyl, alkynyl and aryl groups in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur.

The term "substituted" as in the wording "substituted hydrocarbyl," but also in the wording "substituted alkyl," "substituted aryl," and the like, as alluded to in some of the definitions provided in the present disclosure, means that in the hydrocarbyl, alkyl, aryl, or other moiety, at least one hydrogen atom bound to a carbon (or other) atom is replaced with one or more non-hydrogen substituents. Examples of such substituents include, without limitation functional groups such as, halo, hydroxyl, halides, $C_1$-$C_{20}$ alkoxy, $C_2$-$C_{20}$ alkenyloxy, $C_2$-$C_{20}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{20}$ alkylcarbonyl (—CO-alkyl) and $C_6$-$C_{24}$ arylcarbonyl (—CO-aryl)), acyloxy (—O-acyl, including $C_2$-$C_{20}$ alkylcarbonyloxy (—O—CO-alkyl) and $C_6$-$C_{24}$ arylcarbonyloxy (—O—CO-aryl)), $C_2$-$C_{20}$ alkoxycarbonyl (—(CO)—O-alkyl), $C_6$-$C_{24}$ aryloxycarbonyl (—(CO)—O-aryl), halocarbonyl (—CO)—X where X is halo), $C_{\cdot 2}$-$C_{20}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamido (—NH—(CO)—NH$_2$), carbamoyl (—(CO)—NH$_{\cdot 2}$), mono-($C_1$-$C_{20}$ alkyl)-stituted carbamoyl (—(CO)—NH($C_1$-$C_{20}$ alkyl)), di-($C_1$-$C_{20}$ alkyl)-stituted carbamoyl (—(CO)—N($C_{\cdot 1}$-$C_{20}$ alkyl) $_2$), mono-($C_5$-$C_{24}$ aryl)-stituted carbamoyl (—(CO)—NH-aryl), di-($C_5$-$C_{24}$ aryl)-stituted carbamoyl (—(CO)—N($C_5$-$C_{24}$ aryl)$_{\cdot 2}$), di-N—($C_1$-$C_{20}$ alkyl), N—($C_5$-$C_{24}$ aryl)-stituted carbamoyl, thiocarbamoyl (—(CS)—NH$_2$), mono-($C_1$-$C_{20}$ alkyl)-stituted thiocarbamoyl (—(CO)—NH($C_1$-$C_{20}$ alkyl)), di-($C_1$-$C_{20}$ alkyl)-stituted thiocarbamoyl (—(CO)—N($C_1$-$C_{20}$ alkyl)$_2$), mono-($C_5$-$C_{24}$ aryl)-stituted thiocarbamoyl (—(CO)—NH-aryl), di-($C_5$-$C_{24}$ aryl)-stituted thiocarbamoyl (—(CO)—N($C_5$-$C_{24}$ aryl)$_2$), di-N—($C_1$-$C_{20}$ alkyl), N—($C_5$-$C_{24}$ aryl)-stituted thiocarbamoyl, cyano(—CN), cyanato (—O—CN), thiocyanato (—S—CN), isocyano (—N+.ident.C$^-$), formyl (—(CO)—H), thioformyl (—(CS)—H), amino (—NH$_{\cdot 2}$), mono-($C_{\cdot \cdot 1}$-$C_{\cdot \cdot 20}$ alkyl)-stituted amino, di-($C_1$-$C_{20}$ alkyl)-stituted amino, mono-($C_5$-$C_{24}$ aryl)-stituted amino, di-($C_5$-$C_{24}$ aryl)-stituted amino, $C_2$-$C_{20}$ alkylamido (—NH—(CO)-alkyl), $C_6$-$C_{24}$ arylamido (—NH—(CO)-aryl), imino (—CR.dbd.NH where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR.dbd.N(alkyl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), arylimino (—CR.dbd.N(aryl), where R=hydrogen, $C_{\cdot 1}$-$C_{20}$ alkyl, $C_5$-$C_{24}$ aryl, $C_6$-$C_{24}$ alkaryl, $C_{\cdot 6}$-$C_{24}$ aralkyl, etc.), nitro (—NO$_{\cdot \cdot 2}$), nitroso (—NO), sulfo (—SO$_{\cdot 2}$—OH), sulfonato (—SO$_{\cdot 2}$—O.sup.-), $C_1$-$C_{20}$ alkylsulfanyl (—S-alkyl; also termed "alkylthio"), $C_5$-$C_{24}$ arylsulfanyl (—S-aryl; also termed "arylthio"), $C_1$-$C_{20}$ alkylsulfinyl (—(SO)-alkyl), $C_5$-$C_{24}$ arylsulfinyl (—(SO)-aryl), $C_1$-$C_{20}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O.sup.-)$_{\cdot \cdot 2}$), phosphinato (—P(O)(O$^-$)), phospho (—PO$_2$), phosphino (—PR$_{\cdot \cdot 2}$ where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), silyl (—SiR$_3$ wherein R is hydrogen or hydrocarbyl), and silyloxy (—O-silyl), and the hydrocarbyl moieties $C_1$-$C_{20}$ alkyl (preferably $C_1$-$C_{12}$ alkyl, more preferably $C_1$-$C_6$ alkyl), $C_2$-$C_{20}$ alkenyl (preferably $C_2$-$C_{12}$ alkenyl, more preferably $C_2$-$C_6$ alkenyl), $C_2$-$C_{20}$ alkynyl (preferably $C_2$-$C_{\cdot 12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_16$ alkaryl), and $C_6$-$C_{24}$ aralkyl (preferably $C_6$-$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

The wording "functional group" as described herein indicates a group that contains heteroatoms such as alcohols, amines and substituted amines, thiols, thioethers, ethers, and carbonyls.

The term "cyclic" refers to alicyclic or aromatic substituents that may or may not be substituted and/or heteroatom containing and that might be monocyclic, bicyclic or polycyclic. The term "alicyclic" is used in the conventional sense to refer to an aliphatic cyclic moiety, as opposed to an aromatic cyclic moiety and may be monocyclic, bicyclic or polycyclic.

In the non-metallocene organometallic complexes of formula (II) selection of the metal, first and second substituted aryl and cyclic group (herein also referred as linker) determine the resulting geometries of the non-metallocene organometallic complex of formula (II) via the M-Z bond, the Z-aryl bond, and, in particular, the aryl-linker (aryl-YL) semi-rigid, ring-ring linkages at the at the ortho position with respect to the Z anionic donor. For example in a $C_s$ symmetry aryl rings rotate around the aryl-linker bond in the same direction, in a $C_1$ symmetry only one aryl rotates around the aryl-linker bond, and in a $C_2$ symmetry aryl rings rotate around the aryl-linker bond in opposite directions (FIG. 2).

A $C_2$-symmetric non-metallocene organometallic complex of Formula (II) can be provided when the terminal aryl groups twist away from each other. Various species of $C_2$-symmetric non-metallocene organometallic complex of Formula (II) can be prepared and structurally characterized with various ligand sets as exemplified in examples 1a-TiBn$_2$, 1b-TiBn$_2$, 2-TiBn$_2$, 1c-Ti(OiPr)$_2$, and illustrated in FIGS. 4, 5, 6 8 10 and 11.

Figure 9A:
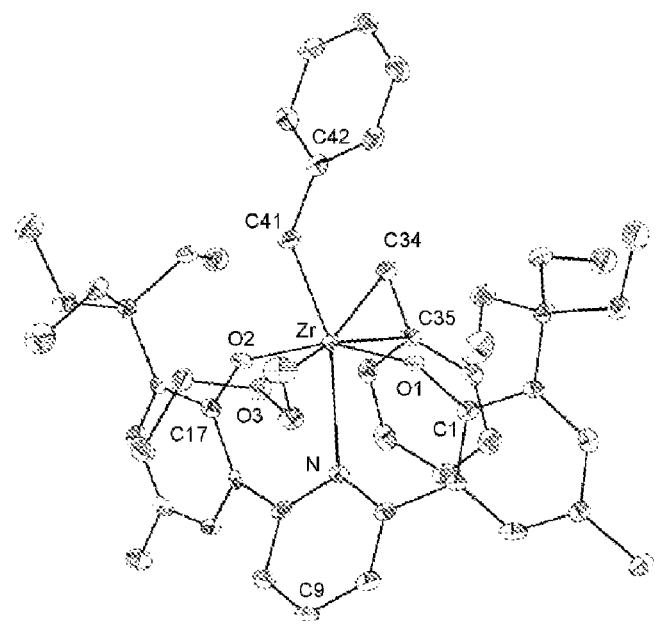
FIGS. 9A and 9B are an illustration of the structure of an exemplary organometallic complex according to an embodiment herein described. View A is roughly perpendicular to the Zr—N vector and view B is along the Zr—N vector.
Figure 9B:
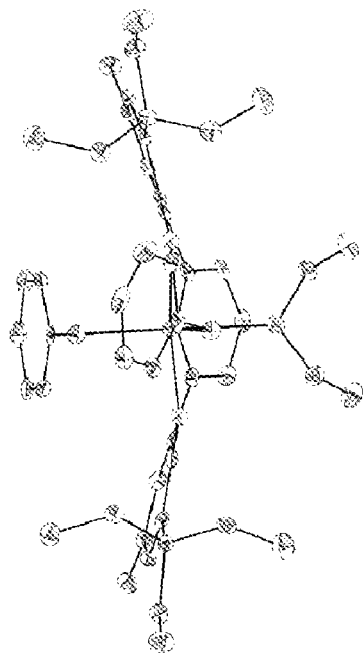
Figure 10A:
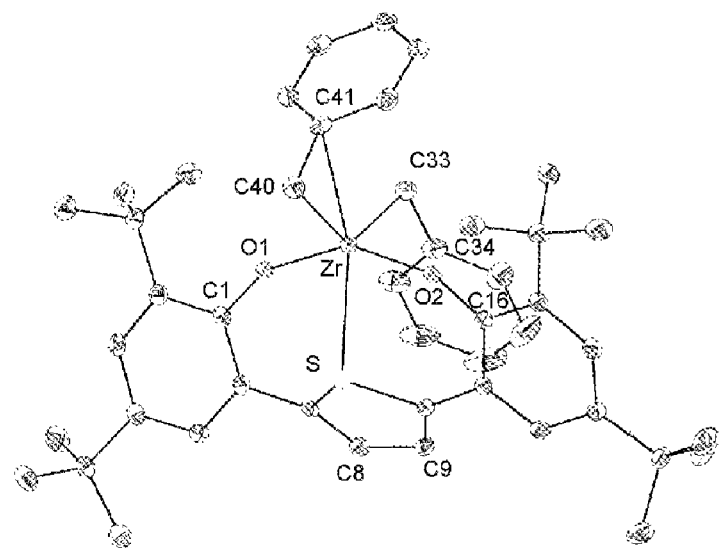
FIGS. 10A and 10B are an illustration of the structure of an exemplary organometallic complex according to an embodiment herein described. View A is roughly perpendicular to the Zr—S vector and view B is along the Zr—S vector.
Figure 10B:
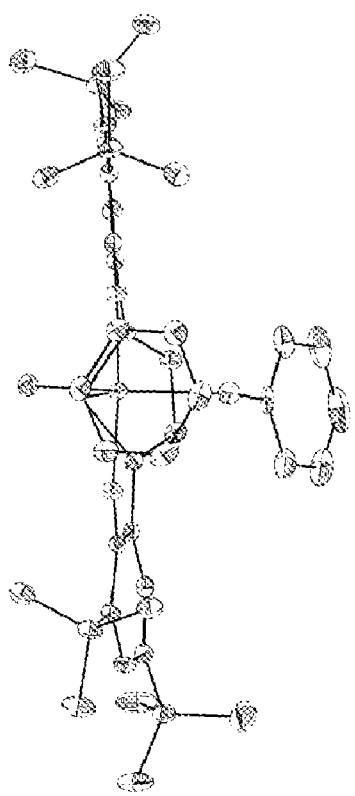
Figure 11A:
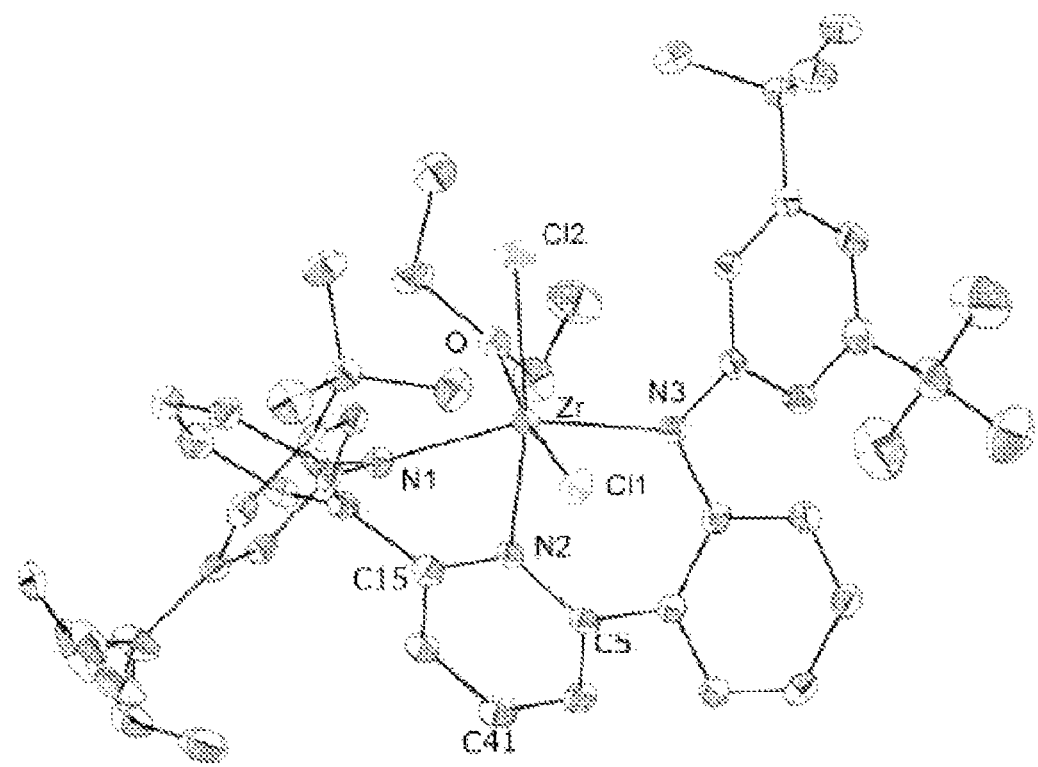
FIGS. 11A and 11B shows a schematic illustration of the structure of an exemplary organometallic complex according to an embodiment herein described. View A is roughly perpendicular to the Ti—N vector and view B is along the Ti—N vector.
Figure 11B:
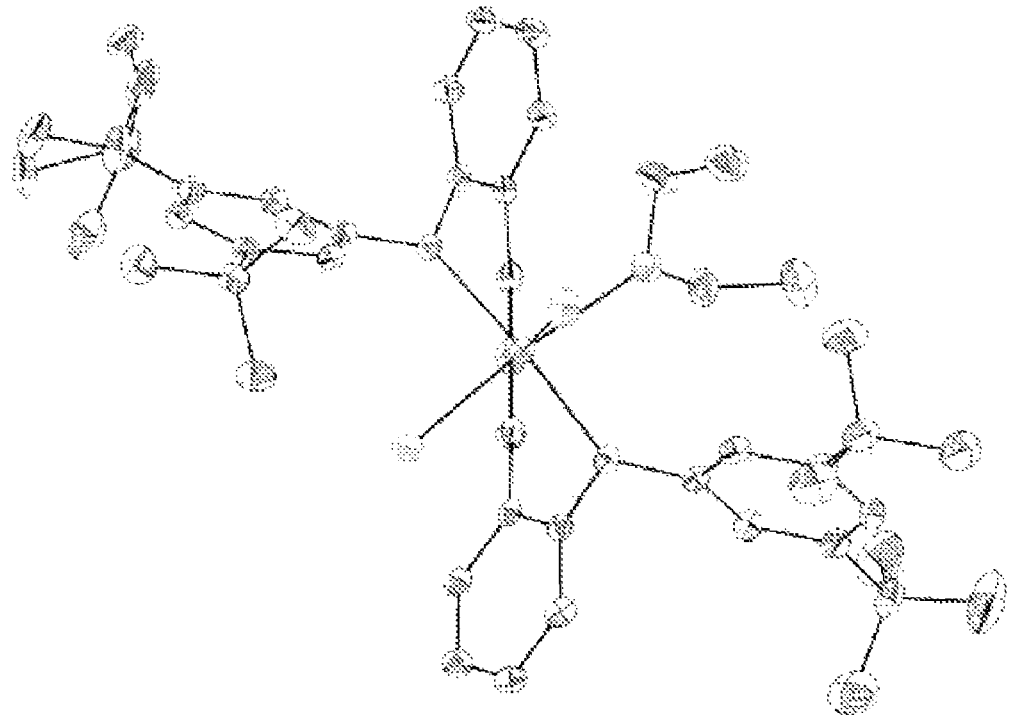
Figure 12A:
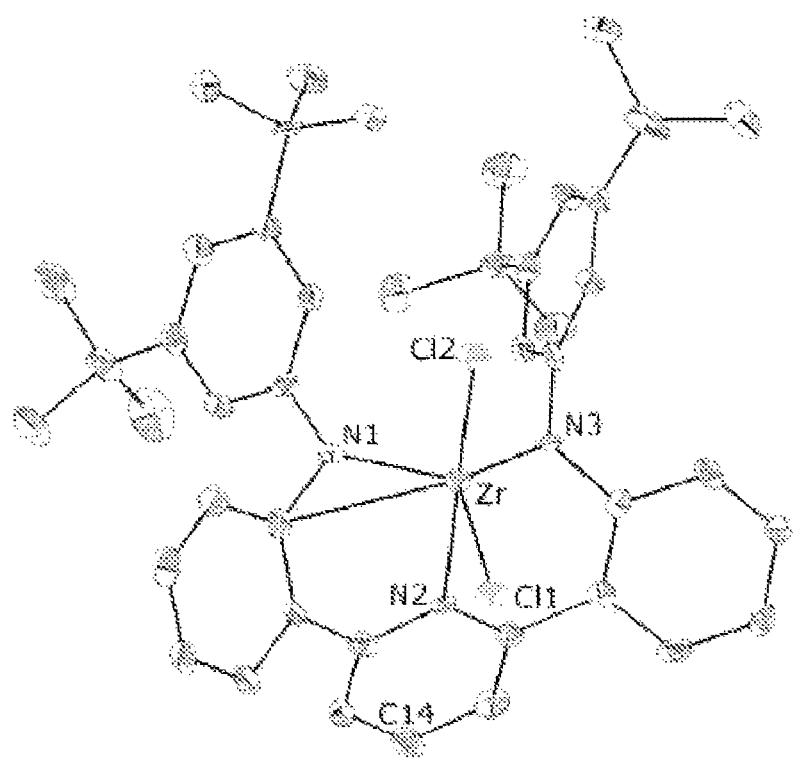
FIGS. 12A and 12B shows a schematic illustration of the structure of an exemplary organometallic complex according to an embodiment herein described. View A is roughly perpendicular to the Ti—N vector and view B is along the Ti—N vector.
Figure 12B:
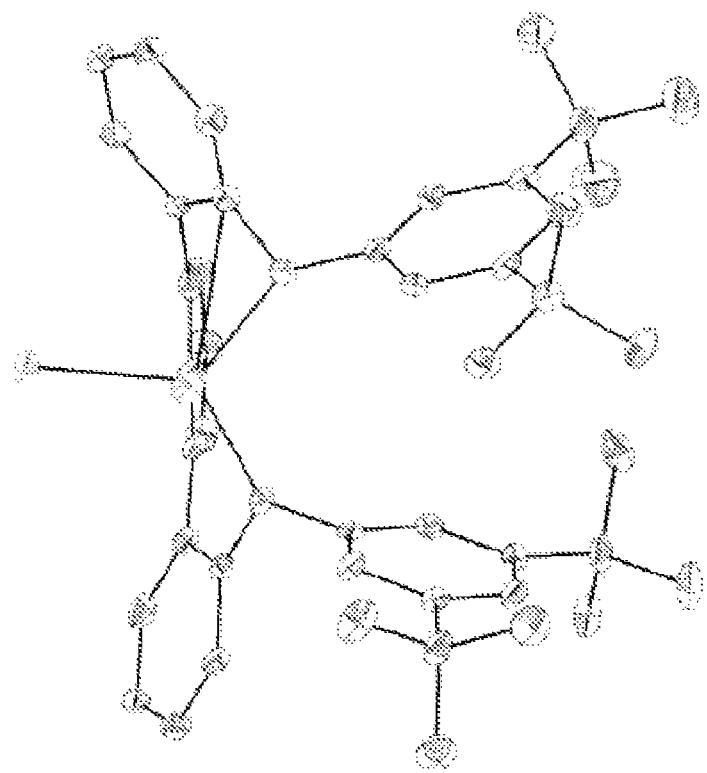

A $C_S$-symmetric non-metallocene organometallic complex of Formula (II) can be provided when the terminal aryl groups twist in the same direction. Various species of $C_S$-symmetric non-metallocene organometallic complex of Formula (II) can be prepared and structurally characterized with various ligand sets as exemplified in examples 1b-ZrBn$_2$, 1c-ZrBn$_2$, 3-ZrBn$_2$, and illustrated in FIGS. 7, 9, and 12.

A $C_{2V}$-symmetric non-metallocene organometallic complex of Formula (II) can be provided when the terminal aryl groups and the linker group are in the same plane. Various species of $C_{2V}$-symmetric non-metallocene organometallic complex of Formula (II) can be prepared and structurally characterized with various ligand sets as would be apparent to the skilled person upon reading of the present disclosure.

A $C_1$-symmetric non-metallocene organometallic complex of Formula (II) can be provided when one the terminal aryl group twists away from the linker group while the other remains in the plane. Various species of $C_1$-symmetric non-metallocene organometallic complex of Formula (II) can be prepared and structurally characterized with various ligand sets as would be apparent to the skilled person upon reading of the present disclosure.

In some embodiments, the non-metallocene organometallic complex herein described is enantiopure. In the non-metallocene organometallic complex of Formula (II), enantiopure species can be obtained achieved in a number of ways;

including but not limited to generation of a $C_2$-symmetric non-metallocene organometallic complex by choosing a suitable M and R' combination (e.g. when M is Ti and each of R, $R_1$ and R' is a bulky group), inclusion of chiral groups in the linker to provide a $C_2$-symmetric non-metallocene organometallic complex, or substitution of the linker or terminal aryl rings with alkyl, aryl, halide, or any other functional groups that can inhibit rotation around the linker-aryl bonds thus providing a $C_2$-symmetric non-metallocene organometallic complex. Enantiopure species of the non-metallocene organometallic complex herein disclosed and in particular enantiopure $C_2$-symmetric non-metallocene organometallic complex of formula (II) can be separated by traditional resolution methods such as diastereomer generation.

In some embodiments, the metal M is a metal selected from the group consisting of group III metals, group IV metals, group V metals, lanthanide metals, and actinide metals In particular, in some embodiments the metal can be selected from the group consisting of aluminum, scandium, yttrium, titanium, zirconium, hafnium, vanadium, niobium, tantalum, chromium and the lanthanides.

In some embodiments, the anionic donors, Z can be anyone of O, S, Se, Te, N, P. As, or Sb, wherein when Z is Te, Se, S, or O, n is 0; and when Z is Sb, As, P, or N, n is 1 and R' can be any organic or inorganic group including but not limited to alkyl, aryl, silyl, boryl. R' can also be a chiral group. Exemplary non metallocene organometallic complexes are herein disclosed wherein Z is O or N and R' is 2,4,6-trimethylphenyl, 3,5-di-t-butylphenyl, and trimethylsilyl are described in the examples section and illustrated in FIGS. 4 to 12.

In some embodiments, the anionic donor Z is N or O and the resulting bisphenolates and bisanilides in the ligand framework are the first and second substituted aryl groups connected at the ortho positions with the ligand L via semi-rigid, ring-ring linkages.

In some embodiments, L is a neutral or an anionic ligand such as a group 14, 15, or 16 element.

In some embodiments, the ligand L is linked to the organic fragment Y to form a ring of various sizes (e.g. has 3 to 10 atoms in the ring), including but not limited to any heterocycle, aryl, or other groups containing donors (donors can be any group 14, 15, 16, or 17 element) or not such as benzene and in particular a flat heterocycle such as substituted or unsubstituted pyridine, furan, or thiophene linkers, and wherein these pyridine, furan, thiophene, or benzene linkers can be in particular substituted with any aryl, alkyl, or other organic groups such as amines, ethers, thioethers, phosphines, or halides.

In particular in some embodiments, L=N, and the cyclic group is a pyridine linker connecting phenoxides (Z=O) for M=titanium zirconium or vanadium.

In some embodiments, L=S or O and the cyclic group is thiophene or furan connecting phenoxides (Z=O) for M=titanium.

In some embodiments, L=O and the cyclic group is furan connecting phenoxides (Z=O) for M=zirconium.

Figure 3A:
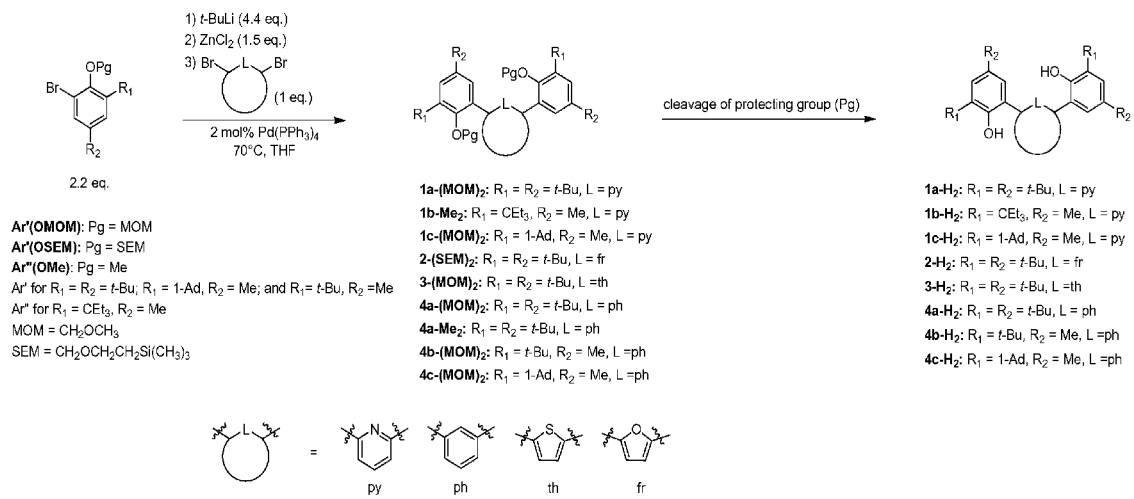
FIG. 3A. shows a schematic illustration of an exemplary reaction scheme (scheme 1) for the preparation of a semi-rigid tridentate ligand framework of organometallic complexes according to an embodiment herein described.

In some embodiments R and $R_1$ are independently an organic group or a functional group including but not limited to alkyl, aryl, silyl, boryl, and halide groups, e.g. tBu, Me, 1-Ad, $CEt_3$ as exemplified in the examples for 1a-$H_2$, 1b-$H_2$, 1c-$H_2$, 2-$H_2$, 3-$H_2$, 4a-$H_2$, 4b-$H_2$, 4c-$H_2$. and illustrated in FIG. 3a In some embodiments, R and $R_1$ are the same. In some embodiments R and/or R1 can be chiral.

In some embodiments, R' and $R'_1$ are independently an organic group or functional group including but not limited to alkyl, aryl, silyl groups such as 2,4,6-trimethylphenyl, 3,5-di-t-butylphenyl, and trimethylsilyl exemplified in examples 6a and 6b. In some embodiments R' and $R'_1$ are the same. In some embodiments, R' and/or $R'_1$ can also be a chiral group.

In some embodiments, R" is a halide such as a fluoride, chloride, bromide, and iodide, an alkyl, an aryl, a hydride, or other anionic ligand such as triflate, carboxylate, amide, alkoxide or a combination thereof. Specific examples include chloride and benzyl groups as exemplified in the examples for 1c-VCl(THF), 1c-$TiCl_2$(THF), 1a-$TiBn_2$, 1b-$TiBn_2$, 1c-$TiBn_2$, 2-$TiBn_2$, 3-$TiBn_2$, 1a-$ZrBn_2$, 1b-$ZrBn_2$, 1c-$ZrBn_2$, 2-$ZrBn_2$, 3-$ZrBn_2$, 4b-$TiBn_2$, 4b-$HfBn_2$, 4c-$HfBn_2$. $_2$. and illustrated in FIG. 3c The size of the R, $R_1$ R' and $R'_1$ substituents is important for controlling chain transfer processes and likely for the tacticity control and catalyst stability. In general, larger substituents reduce chain transfer, are better at stabilizing reactive species, and may have greater interaction with the other reaction partners locking the geometry thus making the reaction more selective (i.e. higher tacticity for the product). Large substituents include, but are not limited to, t-butyl, adamantyl, triethylmethyl, mesityl, 2,6-diisopropylphenyl, anthracenyl, and triptycenyl.

In some embodiments the L' group can be a neutral coordinating group, possibly a solvent, such as ether, amine, phosphine, thioether, phosphine oxide, or ketone, as exemplified for L'=ether (diethyl ether or tetrahydrofuran) in example(s) for 1c-VCl(THF), 1c-$TiCl_2$(THF). $_2$. and illustrated in FIG. 3c.

In some embodiments, the organometallic complexes one of the R" group is a carbene and the corresponding organometallic complex includes an alkylidene. The carbene has the general formula =CR'''R'''' where R''' and R'''' can be hydrogen, hydrocarbyl, substituted hydrocarbyl, heteroatom containing hydrocarbyl, and functional groups. The preparation of an alkylidene was exemplified for tantalum in the examples for 1a-TaBn(CHPh)($PMe_2Ph$). $<_2$. and illustrated in FIG. 13

The non metallocene organometallic complexes herein described can be used for preparing polyolefines (which includes polymerizing or oligomerizing olefins) and in particular poly-α-olefins. The term "polymer" refers to a species comprised of ten or more monomer units, which may be the same or different, and includes copolymers, terpolymers, and the like. The term "oligomer", in contrast, refers to a species having from two to nine monomer units. As used herein, the term "copolymer" refers to a polymer having two or more different monomer units. The term "monomer" or "monomer unit" refer to the olefin or other monomer compound before it has been polymerized; the term "monomer units" refer to the moieties of a polymer that correspond to the monomers after they have been polymerized.

In some embodiments the monomer unit can be a $C_3$ to $C_{12}$ functionalized or unfunctionalized α-olefin and in particular a $C_3$ to $C_8$ functionalized or unfunctionalized α-olefin.

The terms "polar olefins" and "functionalized olefin", unless otherwise noted, are used interchangably herein and refer to olefins containing at least one heteroatom such as N, O, S, P, and the like, including but not limited to olefins substituted with oxirane groups, 2,5-dihydrofuran, mono- or di-oxy-substituted butenes, etc., whether as a monomer or a monomer unit of a polymer.

In some embodiments, olefins can be polymerized including but not limited to ethylene, propylene, butanes, pentenes, hexenes, octenes, styrenes, 1,3 butadiene, norbornene and combinations thereof. In particular, ethylene, propylene, 1-hexene, 1-octene, styrene and norbornene can be polymerized. In some embodiments, the non-metallocene organometallic complexes herein described are used for providing olefin homopolymers.

In some embodiments, a $C_2$-symmetric organometallic complex herein described can be used to provide isotactic polyolefins and in particular isotactic poly-α-olefins. In some embodiments, a $C_S$-symmetric organometallic complex herein described can be used to provide atactic polyolefins and in particular atactic poly-α-olefins. In some embodiments, a $C_{2v}$-symmetric organometallic complex herein described can be used to provide atactic polyolefins and in particular atactic poly-α-olefins.

In some embodiments, a $C_1$-symmetric organometallic complex herein described, wherein the organometallic complex is symmetrical, can be used to provide isotactic and/or atactic polyolefins and in particular isotactic and/or atactic poly-α-olefins. In some embodiments, a $C_1$-symmetric organometallic complex herein described, wherein the organometallic complex is unsymmetrical, can be used to provide syndiotactic polyolefins and in particular syndiotactic poly-α-olefins.

In some embodiments wherein the $C_2$-symmetric structure can convert into a $C_S$-symmetric structure during the course of the polymerization (the aryl groups twist in the same direction) by way of modifying reaction conditions such as solvent or temperature, the non-metallocene organometallic complexes herein described can be used to provide a stereoblock copolymer comprising alternating isotactic and atactic blocks. In particular, in some embodiments, a $C_S$-symmetric non-metallocene organometallic complex comprising a 5 coordinated metal, when contacted with a coordinated solvent molecule such as ether, THF and additional solvent identifiable by the skilled person, becomes a $C_2$-symmetric non-metallocene organometallic complex comprising a 6 coordinated metal.

In some embodiments, non-metallocene organometallic complexes with pyridine (L=N) linkers connecting phenoxides (Z=O) for M=titanium and vanadium can give high molecular weight polypropylene in the range of $M_W$=500,000 to 700,000 for titanium and $M_W$=1,100,000 to 1,400,000 for vanadium. The activity of these titanium complexes can be about $1.6 \times 10^4$ g polymer per mol cat·h. The activity of these vanadium complexes can be about $8 \times 10^5$ g polymer per mol cat·h.

As used in the present disclosure the wording "low molecular weight" as used herein with reference to a polymer indicates a polymer with MW<about 1000, while the wording "high molecular weight" as used herein with reference to a polymer indicates a polymer with MW>about 1000.

In some embodiments, non-metallocene organometallic complexes with thiophene and furan (L=S, O) linkers connecting phenoxides (Z=O) for M=titanium can give low molecular weight polypropylene ($C_9$ to $C_{33}$). The activities of these type of complexes for the polymerization of propylene can be approximately about $1.5 \times 10^5$ g polymer per mol cat·h and about $3 \times 10^5$ g polymer per mol cat·h, respectively.

In some embodiments, non-metallocene organometallic complexes with pyridine (L=N) linkers connecting phenoxides (Z=O) for zirconium can give intermediate molecular weight polypropylene (($M_W$=100,000 to 200,000). The activity of these complexes depends on the ortho substituent such that for R=adamantyl, the activity can be about $5 \times 10^5$ g polymer per mol cat·h, when R=t-butyl, the activity can be about $9 \times 10^5$ g polymer per mol cat·h, and when R=triethylmethyl, the activity can be about $1 \times 10^6$ g polymer per mol cat·h.

In some embodiments, non-metallocene organometallic complexes with furan (L=O) linkers connecting phenoxides (Z=O) for zirconium can give a low molecular weight polypropylene fraction ($C_9$ to $C_{45}$). The activity of these complexes can be about $4 \times 10^6$ g polymer per mol cat·h.

In some embodiments, non-metallocene organometallic complexes with pyridine (L=N) linkers connecting phenoxides (Z=O) for M=titanium can be used in 1-hexene polymerization. Activity increased with increasing monomer concentration such that the highest activity can be about $2.5 \times 10^5$ g polymer per mol cat·h.

In some embodiments, non-metallocene organometallic complexes with pyridine (L=N) linkers connecting phenoxides (Z=O) for M=Ti, Zr, and V can be used for ethylene/1-octene copolymerization. In some specific embodiments comonomer incorporation the highest 1-octene content observed for the vanadium precatalyst can be about 6.3%.

In some embodiments, non-metallocene organometallic complexes with pyridine (L=N) connecting phenoxides (Z=O) for titanium which exhibit $C_2$-symmetry in the solid state give isotactic propylene.

In some embodiments, non-metallocene organometallic complexes with pyridine (L=N) connecting phenoxides (Z=O) for zirconium and vanadium which exhibit $C_S$-symmetry in the solid state give atactic propylene.

In some embodiments, a method for polymerizing olefin and in particular α-olefins is provided, the method comprising the step of contacting an olefin with a non-metallocene organometallic complex herein described. In some embodiments, the olefin and the organometallic complex are contacted in presence of a solvent.

In some embodiments, the olefin is contacted with an organometallic complex in presence of an activator. In particular, in embodiments wherein the tridentated ligand of the non-metallocene organometallic complexes is a dianionic ligand (x=2) polymerization is performed in presence of an activator.

In those embodiments, the organometallic complex and the activator are part of a catalyst system. In a preferred embodiment the activator is methylaluminoxane (MAO). Other activators include modified MAO, trityl borate ([Ph$_3$C][B(C$_6$H$_3$(CF$_3$)$_2$)$_4$]), fluorinated boranes (B(C$_6$F$_5$)$_3$), and anilinium borate ([PhNHMe$_2$][B(C$_6$F$_5$)$_4$]). Chain transfer agents such as aluminum alkyls (AlMe$_3$, AlEt$_3$, etc) or zinc alkyls (ZnEt$_2$, ZnMe$_2$, etc) may also be used. In some cases (when L can become an anionic donor), the catalyst may be self initiating, not requiring the addition of an activator. If R" is alkyl or aryl, all of the above activators are acceptable. If R" is halide, MAO or modified MAO are preferred. In most cases, MAO will be the preferred activator.

In embodiments wherein the tridentate ligand of the non-metallocene organometallic complexes is a trianionic ligand (x=3) polymerization can be performed in absence of an activator.

The catalysts and catalyst system are used with or without an inorganic solid or organic polymer support. Suitable supports include silica, alumina, magnesia, titania, clays, zeolites, polymeric supports such as polyethylene, polypropylene, polystyrene, functionalized polystyrene and the like. The supports can be pretreated thermally or chemically to improve catalyst productivity or product properties. The catalysts and/or activators can be deposited on the support in any desired manner. For instance, the catalyst can be dissolved in solvent, combined with a support, and stripped. Alternatively, an incipient-wetness technique can be used. Moreover, the support can simply be introduced into the reactor separately from the catalyst.

In some embodiments organometallic complexes wherein titanium or vanadium is supported by a tridentate ligand including a 6 membered cyclic group, e.g. pyridine bisphenolate ligand are particularly suitable as catalysts for producing high molecular weight polyolefins. In some embodiments, organometallic complexes wherein titanium is supported by a tridentate ligand including a 5 membered cyclic group, e.g. a furan or thiophene bisphenolate ligand are particularly suitable as catalysts for producing low molecular weight polyolefins.

In the exemplary embodiments wherein the organometallic complexes are used as catalysts in propylene polymerization, a pressure resistant vessel is charged with various amounts of MAO (with values of 100 to 10000 Al atoms per precatalyst metal atom, preferred equivalents are in the range of 500 to 4000 Al atoms per precatalyst metal atom) and solvent (preferred solvents are aliphatic and aromatic hydrocarbons and in particular toluene, 2 mL to 30 mL) and fitted with a pressure regulator with a Swagelok quick connect valve and septum. The vessel was sealed and attached to a propylene tank and purged. The olefin was added and the temperature (preferred temperatures are −80° C. to 150° C. and in particular −20° C. to 100° C.) of the vessel was regulated with a bath (oil or water depending on the temperature). The catalyst is dissolved in aliphatic and aromatic hydrocarbon solvents, particularly toluene, and injected into the vessel. The reaction mixture was mixed vigorously for the desired amount of time.

In some embodiments, wherein the non-metallocene organometallic complex herein described includes an alkylidene, the non-metallocene organometallic complex is anticipated to be suitable as catalysts in olefin metathesis including Ring Opening Metathesis Polymerization (ROMP). In particular, non-metallocene organometallic complexes of formula (II) wherein one of the R" group is a carbene and the corresponding organometallic complex includes an alkylidene, are anticipated to be suitable in olefin polymerization metathesis reactions, Olefin polymerization metathesis reactions, and in particular ROMP reactions are known in the art and identifiable by a skilled person and will not herein be described in further details In some embodiments, olefin polymerization can be performed via organometallic transformations such as C—H bond activation to provide a cyclometallated product, in the absence of activators, and with non-metallocene organometallic complexes such as non-metallocene organometallic complexes wherein L is an anionic donor and L and Y are linked to form a phenyl group.

In some embodiments, non-metallocene organometallic complexes herein described can be used as Lewis acid in any reactions performed in presence of a Lewis acid, (a Lewis acid is included in the reaction mixture). Reactions that involve a Lewis acid are known in the art and identifiable by a skilled person and will not herein be described in further details.

The non-metallocene organometallic complex herein disclosed can be prepared using well documented procedures. Starting from commercially available or easily accessible reagents such as o-bromophenols or o-bromoanilines, the desired linked frameworks can be generated using coupling chemistry, (e.g. catalyzed by palladium), wherein the coupling partner can be a doubly brominated "linker" which is thus connected to two substituted aryl groups such as phenols or anilines. Suitable protecting groups are used for functionalities, such as phenol functionality and consequently removed after the sensitive steps.

In some embodiments, the organometallic complex herein disclosed can be prepared by a condensation reaction in which the linker is cyclized from a linear precursor bearing groups such as o-phenols or o-anilines at the extremities. The tridentate ligand such as the tridentate ligand of formula (I) can then be bound to a metal, such as an early transition metal, by salt metathesis, alcohol elimination, alkane elimination, or amine elimination to give a complex such as the complex of formula (II).

The disclosure is further illustrated in the following examples, which are provided by way of illustration and are not intended to be limiting

EXAMPLES

General Considerations and Instrumentation

All air- and moisture-sensitive compounds were manipulated under argon or nitrogen using standard glovebox, Schlenk, and high-vacuum line techniques. (Burger, B. J.; Bercaw, J. E. In *Experimental Organometallic Chemistry: A Practicum in Synthesis and Characterization*, Vol. 357; Wayda, A. L., Darensbourg, M. Y, Eds.; American Chemical Society; Washington D.C.; 1987; pp 79-98.) Argon was purified and dried by passage through columns of MnO on vermiculite and activated 4 Å molecular sieves. Solvents were dried over sodium benzophenone ketyl (THF, $Et_2O$), titanocene (toluene), or by the method of Grubbs. (Marvich, R. H.; Brintzinger, H. H. *J. Am. Chem. Soc.* 1971, 93, 2046 and Pangborn, A. B.; Giardello, M. A.; Grubbs, R. H.; Rosen, R. K.; Timmers, F. J. *Organometallics* 1996, 15, 1518-20.) Benzene-$d_6$ was purchased from Cambridge Isotopes and distilled from sodium benzophenone ketyl. Chloroform-$d_1$ and chlorobenzene-$d_5$ were purchased from Cambridge Isotopes and distilled from calcium hydride.

All chemicals were purchased and used as received from Aldrich except methylaluminoxane (MAO) which was purchased from Albemarle. The MAO was dried in vacuo at 150° C. overnight to remove free trimethylaluminum before use. Propylene was dried by passage through a Matheson 2110 drying system equipped with an OXISORB column. $^1H$ and $^{13}C$ NMR spectra were recorded on Varian Mercury 300 or Varian INOVA-500 spectrometers and unless otherwise indicated at room temperature. Chemical shifts are reported with respect to internal solvent: 7.16 and 128.38 (t) ppm ($C_6D_6$); 7.27 and 77.23 (t) ppm ($CDCl_3$); 5.32 and 54.00 (q) ppm ($CD_2Cl_2$); 6.0 and 73.78 (t) ppm ($C_2D_2Cl_4$); for $^1H$ and $^{13}C$ data. Gas chromatographs (GC) were obtained on an Agilent 6890 Series gas chromatograph by using a 30 m×0.25 mm polysiloxane "HP-5" column from Agilent Technologies for monomer conversions. Analysis by GC-MS was carried out on an HP 5890 Series II gas chromatograph connected to an HP 5972 mass spectrometric detector. A 60 m×0.32 μm internal diameter column was used which was coated with a 5 μm think 100% methylsiloxane film.

Dynamic scanning calorimetry (DSC) thermographs were obtained on a PerkinElmer (Wellesley, Mass.) DSC-7 using the Pyris software package for data analysis. Crystallization and melting temperatures were obtained after erasing thermal history by multiple heating and cooling cycles. 2-Adamantyl-4-methylphenol (Gademann, K.; Chavez, D. E.; Jacobsen, E. N. *Angew. Chem. Int. Ed.* 2002, 41, 3059-3061.), $TiCl_4(THF)_2$, $VCl_3(THF)_3$ (Manzer, L. E. *Inorg. Syn.* 1982, 21, 135-140.), tetrabenzyl titanium, tetrabenzyl zirconium, and tetrabenzyl hafnium (Zucchini, U.; Giannini, U.; Albizzati, E.; D'Angelo, R. *J. Chem. Soc. Chem. Comm.* 1969, 20, 1174-1175.) were prepared according to literature procedures.

Example 1

Preparation of Bisphenol Ligands (Scheme 1, FIG. 3a)

Preparation of Bisphenols

The present bisphenols have been prepared using well precedented procedures. Starting from commercially available and inexpensive p-cresol or 2,4-di-t-butyl phenol, the desired linked bisphenols can be accessed within four steps. Bromination and suitable protection of the phenol functionality generates precursors for palladium coupling chemistry (Scheme 1 FIG. 2A). Lithium-halogen exchange followed by salt metathesis with $ZnCl_2$ provides aryl zinc reagents suitable for the Negishi cross-couping. 2,6-Dibromopyridine, 2,5-dibromothiophene, 1,3-dibromobenzene and 2,5-dibromofuran have been used as coupling partners with $Pd(PPh_3)_4$ as catalyst. Aqueous workup provides protected bisphenols as white powders. Methoxymethyl (MOM) and methyl protecting groups have been used for making the pyridine and thiophene linked systems. Standard deprotecting procedures—acidic methanol at 80° C., NaSEt in DMF at 110° C.—have been employed for removing MOM and Me groups, respectively. For the furan linked system, acid catalyzed removal of MOM groups proved difficult, leading to multiple products. Utilization of SEM protecting groups allowed both the palladium catalyzed coupling reaction and clean deprotection using $Bu_4NF$ in HMPA. Analytically pure bisphenols are obtained as white solids by precipitation from methanol and collection by filtration.

Synthesis of 1-methoxymethylether-2,4-di-t-butyl-6-bromobenzene

Bromine (3.7 mL, 11.6 g, 72.5 mmol, 1 equiv) was added via syringe to a solution of 2,4-di-t-butyl-phenol (15 g, 72.8 mmol, 1 equiv) in $CH_2Cl_2$ (200 ml). The brown color of $Br_2$ disappeared upon addition. GC-MS analysis after 5 min shows only the presence of the desired brominated product ($M^+$=286). The organic mixture was washed with water, then dried over $MgSO_4$, and filtered. Upon removal of volatile material by rotary evaporation, a golden oil was obtained which solidified after placing under high vacuum (<1 mTorr). This material (4,6-di-t-butyl-2-bromophenol) was dissolved in dry THF (200 mL), under argon, and was deprotonated with NaH (1.92 g, 80 mmol, 1.1 equiv). After the addition of NaH the reaction mixture was stirred for 1 h at room temperature then MOMCl (6.1 mL, 6.5 g, 80.3 mmol, 1.1 equiv) was added via syringe. The reaction mixture was stirred at room temperature for 9 h. Water was added and the mixture was concentrated under vacuum to remove the THF. The desired product was extracted with $CH_2Cl_2$ (three times). The combined organic fractions were dried over $MgSO_4$, filtered, and concentrated to ~50 mL. $CaH_2$ was added and stirred at room temperature for 6 h then at 100° C., under vacuum, for 1 h. The reaction vessel was sealed with a needle valve and brought inside an inert atmosphere glove box. The mixture was filtered through a pad of activated alumina with the aid of some $Et_2O$. Volatiles were removed under vacuum to give 23.5 g (98% yield over two steps) of desired product 1-methoxymethylether-2,4-di-t-butyl-6-bromobenzene, as a golden oil. $^1H$ NMR (300 MHz, $CDCl_3$) δ: 1.30 (s, 9H, $C(CH_3)_3$), 1.44 (s, 9H, $C(CH_3)_3$), 3.70 (s, 3H, $OCH_3$), 5.23 (s, 2H, $OCH_2O$), 7.32 (d, 2H, aryl-H, $^4J$=2.4 Hz), 7.41 (d, 2H, aryl-H, $^4J$=2.4 Hz). $^{13}C$ NMR (75 MHz, $CDCl_3$) δ: 31.0 ($C(CH_3)_3$), 31.5 ($C(CH_3)_3$), 34.8 ($C(CH_3)_3$), 36.1 ($C(CH_3)_3$), 57.9 ($OCH_3$), 99.5 ($OCH_2O$), 117.7, 124.1, 128.9, 144.6, 147.8, 150.7 (aryl). GC-MS: $M^+$=328.

Synthesis of 1-methoxy-2,4-di-t-butyl-6-bromobenzene

A procedure analogous the synthesis of 1-methoxymethylether-2,4-di-t-butyl-6-bromobenzene was employed. The MOMCl was replaced with $Me_2SO_4$ as alkylating agent. Starting from 20 g of 2,4-di-t-butyl-phenol, 26.8 g (92% yield over two steps) of 1-methoxy-2,4-di-t-butyl-6-bromobenzene were obtained. $^1H$ NMR (300 MHz, $CDCl_3$) δ: 1.30 (s, 9H, $C(CH_3)_3$), 1.41 (s, 9H, $C(CH_3)_3$), 3.92 (s, 3H, $OCH_3$), 7.29 (d, 2H, aryl-H, $^4J$=2.3 Hz), 7.42 (d, 2H, aryl-H, $^4J$=2.3 Hz). $^{13}C$ NMR (75 MHz, $CDCl_3$) δ: 31.1 ($C(CH_3)_3$), 31.6 ($C(CH_3)_3$), 34.8 ($C(CH_3)_3$), 35.9 ($C(CH_3)_3$), 61.5 ($OCH_3$), 117.8, 123.8, 129.0, 144.2, 147.4, 154.3 (aryl). GC-MS: $M^+$=298.

Synthesis of 2-t-butyl-4-methyl-6-bromophenol 2-t-Butyl-4-methylphenol (10 g, 60.8 mmol) is dissolved in $CH_2Cl_2$ (300 mL). Bromine (3.1 mL, 60.8 mmol) is added dropwise to the solution. After 20 minutes, the crude mixture is washed with $H_2O$, dried over $MgSO_4$, filtered and rotovapped to give yellow oil: 12.6 g, 85%. $^1H$ NMR ($CDCl_3$) δ: 1.402 (s, 9H, t-Bu), 2.267 (s, 3H, $CH_3$), 5.640 (s, 1H, OH), 7.017 (s, 1H, Ar), 7.167 (s, 1H, Ar).

Synthesis of 2-adamantyl-4-methyl-6-bromophenol

This compound was prepared in an analogous manner to 2-t-butyl-4-methyl-6-bromophenol to give a pale yellow solid: 10.6 g, 80%. $^1H$ NMR ($CDCl_3$) δ: 1.772 (s, 6H, Ad), 2.099 (s, 9H, Ad), 2.254 (s, 3H, $CH_3$), 5.625 (s, 1H, OH), 6.954 (s, 1H, Ar), 7.155 (s, 1H, Ar).

Protection of 2-t-butyl-4-methyl-6-bromophenol

Sodium hydride (1.48 g, 61.9 mmol) is suspended in anhydrous THF (30 mL). 2-t-Butyl-4-methyl-6-bromophenol (12.6 g, 51.6 mmol) is dissolved in anhydrous THF (200 mL) and cannulated onto the sodium hydride suspension whereupon hydrogen gas is evolved. After 3.5 hours, chloromethyl methylether (4.3 mL, 56.8 mmol) is syringed into the reaction flask. The mixture is stirred for 14 hours. The mixture is concentrated, extracted in $H_2O$, washed with diethyl ether (50 mL, 3×), dried over $MgSO_4$, filtered and rotovapped to give goldenrod-colored oil: 12.7 g, 86%. $^1H$ NMR ($CDCl_3$) δ: 1.424 (s, 9H, t-Bu), 2.280 (s, 3H, $CH_3$), 3.694 (s, 3H, $CH_3$), 5.210 (s, 2H, $CH_2$), 7.089 (s, 1H, Ar), 7.246 (s, 1H, Ar).

Protection of 2-adamantyl-4-methyl-6-bromophenol

This compound is prepared analogously to 1-methoxylmethylether-2-t-butyl-4-methyl-6-bromobenzene. The crude product is purified by Kugelrohr distillation to give a white solid: 5.2 g, 71%. $^1H$ NMR ($CDCl_3$) δ: 1.768 (s, 6H, Ad), 2.102 (s, 9H, Ad), 2.269 (s, 3H, $CH_3$), 3.705 (s, 3H, $CH_3$), 5.211 (s, 2H, $CH_2$), 7.083 (s, 1H, Ar), 7.260 (s, 1H, Ar).

Synthesis of phenyl-1,5-bis(2,4-di-t-butylphenol) (4a-$H_2$)

A mixture of 1-methoxy-2,4-di-t-butyl-6-bromobenzene (8.0 g, 26.8 mmol, 1 equiv) and THF (100 mL) in a Schlenk tube fitted with a screw-in Teflon stopper was frozen in a cold well, in an inert atmosphere glove box. This mixture was allowed to thaw and t-BuLi solution (1.7 M in pentanes, 33 mL, 56.1 mmol, 2.1 equiv) was added via syringe. The mixture was stirred for 1 h, the allowed to reach room temperature. $ZnCl_2$ (2.6 g, 20 mmol, 0.7 equiv) was added with the aid of 25 mL THF. After stirring the reaction mixture for 30 minutes, 1,3-dibromobenzene (2.84 g, 12.0 mmol, 0.45 equiv) and $Pd(PPh_3)_4$ (0.31 g, 0.27 mmol, 0.01 equiv) with the aid of some THF (~25 mL). The reaction vessel was placed in an oil bath preheated to 75° C. Upon stirring for 16 h the mixture was allowed to cool to room temperature and was quenched with water. Volatile materials were removed under vacuum and water was added (~150 mL). This mixture was extracted with $Et_2O$ (three times). The combined organics were dried over $MgSO_4$, filtered, and concentrated by rotary evaporation. The resulting residue was suspended in MeOH and cooled to −25° C. The white precipitate was collected by filtration through a sintered glass funnel and washed with cold MeOH.

This procedure generates 5.6 g of 4a-$Me_2$ as a white powder. $^1H$ NMR (300 MHz, $CDCl_3$) δ: 1.35 (s, 18H, $C(CH_3)_3$), 1.45 (s, 18H, $C(CH_3)_3$), 3.34 (s, 6H, $OCH_3$), 7.22 (d, 2H, aryl-H, $^4J$=2.5 Hz), 7.36 (d, 2H, aryl-H, $^4J$=2.5 Hz), 7.45-7.51 (m, 1H, 5-$C_6H_3$—H), 7.56 (app dt, 2H, 4,6-$C_6H_2$—$H_2$), 7.81 (app t, 1H, 2-$C_6H_3$—H). $^{13}C$ NMR (75 MHz, $CDCl_3$) δ: 31.2 ($C(CH_3)_3$), 31.8 ($C(CH_3)_3$), 34.8 ($C(CH_3)_3$), 35.6 ($C(CH_3)_3$), 60.4 ($OCH_3$), 123.6, 126.9, 127.8, 128.6, 130.0, 134.6, 140.9, 142.2, 145.6, 155.2 (aryl). GC-MS: $M^+$=514. Compound 4a-$Me_2$ (5.6 g, 10.9 mmol, 1 equiv) obtained above was suspended in DMF (60 mL). (Greene, T. W.; Wuts, P. G. M. *Protective Groups in Organic Synthesis*; Wiley & Sons: New York, 1999.) NaSEt was prepared in situ by the slow addition of EtSH (3.2 mL, 2.7 g, 43.3 mmol, 4 equiv) and NaH (1.04 g, 43.3 mmol, 4 equiv). The resulting mixture was heated to 110° C. for 5 hours, then cooled and an aliquot was collected and inspected by GC-MS to show the formation of the free phenol ($M^+$=486). Water (60 mL) was added and the resulting mixture was extracted with $Et_2O$, dried over $MgSO_4$, and filtered. Volatile materials were removed by rotary evaporation with mild heating. The residue was triturated with MeOH a couple of times, then suspended in MeOH (20 mL) and cooled to −25° C. A white precipitate was collected by filtration and washed with cold MeOH. The collected solid was placed under vacuum to give 4.77 g (9.8 mmol, 81% yield over two steps) desired product 4a-$H_2$.

Preparation of 4a-$H_2$ using 1-methoxymethylether-2,4-di-t-butyl-6-bromobenzene as the starting material involves an analogous palladium coupling to give the terphenyl framework 4a-$(MOM)_2$. This material was carried over to the step involving removal of protecting group. Compound 4a-$(MOM)_2$ was suspended in MeOH and concentrated HCl was added. This mixture was heated at 80° C. for 2-6 h. Upon cooling down, volatile materials were removed under vacuum and the desired product (4a-$H_2$) was obtained as above. Starting from 1.24 g of 1,3-dibrombenzene led to the isolation of 1.83 g (72% yield) of 4a-$H_2$. $^1H$ NMR (300 MHz, $CDCl_3$) δ: 1.36 (s, 18H, $C(CH_3)_3$), 1.49 (s, 18H, $C(CH_3)_3$), 5.51 (s, 2H, OH), 7.15 (d, 2H, aryl-H, $^4J$=2.5 Hz), 7.39 (d, 2H, aryl-H, $^4J$=2.5 Hz), 7.55 (app dt, 1H, 2H, 4,6-$C_6H_2$—$H_2$), 7.61-7.66 (m, 2H, 2,5-$C_6H_2$—$H_2$). $^{13}C$ NMR (75 MHz, $CDCl_3$) δ: 30.0 ($C(CH_3)_3$), 31.9 ($C(CH_3)_3$), 34.6 ($C(CH_3)_3$), 35.4 ($C(CH_3)_3$), 124.3, 125.0, 127.8, 129.0, 130.4, 131.1, 135.9, 139.5, 142.5, 148.9 (aryl).

Preparation of AR'(OSEM)

A procedure similar to the preparation of 4a-$(MOM)_2$ was utilized. Yield 90% (16.9 g) starting from 2-bromo-4,6-di-t-butyl-phenol. $^1H$ NMR (300 MHz, $CDCl_3$) δ: 0.07 (s, 9H, $Si(CH_3)_3$), 1.06 (s, 2H, $OCH_2CH_2Si$), 1.30 (s, 9H, $C(CH_3)_3$), 1.44 (s, 9H, $C(CH_3)_3$), 3.98 (s, 2H, $OCH_2CH_2Si$), 5.26 (s, 2H, $OCH_2O$), 7.31 (d, 2H, aryl-H), 7.40 (d, 2H, aryl-H). $^{13}C$ NMR (75 MHz, $CDCl_3$) δ: −1.2 ($Si(CH_3)_3$), 18.4 ($SiCH_2$), 31.1 ($C(CH_3)_3$), 31.5 ($C(CH_3)_3$), 34.8 ($C(CH_3)_3$), 36.1 ($C(CH_3)_3$), 67.8 ($OCH_2CH_2$), 97.8 ($OCH_2O$), 117.8, 124.1, 128.9, 144.6, 147.6, 150.7 (aryl).

Preparation of Protected Bisphenols

A procedure analogous to that for 4a-$(MOM)_2$ was employed.

1a-$(MOM)_2$. $^1H$ NMR (300 MHz, $CDCl_3$) δ: 1.37 (s, 18H, $C(CH_3)_3$), 1.51 (s, 18H, $C(CH_3)_3$), 3.41 (s, 6H, $OCH_3$), 4.64 (s, 4H, $OCH_2O$), 7.45 (d, 2H, aryl-H), 7.61 (d, 2H, aryl-H), 7.68-7.80 (m, 3H, $NC_5H_3$). $^{13}C$ NMR (75 MHz, $CDCl_3$) δ: 31.1 ($C(CH_3)_3$), 31.6 ($C(CH_3)_3$), 34.8 ($C(CH_3)_3$), 35.6 ($C(CH_3)_3$), 57.6 ($OCH_3$), 99.7 ($OCH_2O$), 123.2, 125.2, 126.7, 134.1, 136.1, 142.5, 146.1, 151.5, 158.4 (aryl).

1b-$Me_2$. $^1H$ NMR (300 MHz, $CDCl_3$) δ: 0.70 (t, 9H, $CH_2CH_3$), 1.85 (q, 6H, $CH_2CH_3$), 2.37 (s, 3H, aryl-$CH_3$), 3.32 (s, 6H, $OCH_3$), 7.05 (d, 2H, aryl-H), 7.42 (d, 2H, aryl-H), 7.65-7.75 (m, 3H, $NC_5H_3$). $^{13}C$ NMR (75 MHz, $CDCl_3$) δ: 8.7 ($CH_2CH_3$), 21.4 (aryl-$CH_3$), 27.1 ($CH_2CH_3$), 44.9 (aryl-C), 61.0 ($OCH_3$), 123.0, 130.2, 131.0, 132.4, 134.2, 136.2, 138.7, 155.8, 158.2 (aryl).

1c-$(MOM)_2$. $^1H$ NMR ($CDCl_3$) δ: 1.795 (s, 12H, Ad), 2.114 (s, 6H, Ad), 2.186 (s, 12H, Ad), 2.343 (s, 6H, $CH_3$), 3.377 (s, 6H, $OCH_3$), 4.582 (s, 4H, $OCH_2O$), 7.141 (s, 2H, Ar), 7.327 (s, 2H, Ar) 7.602 (d, 2H, py), 7.754 (t, 1H, py).

2-$(SEM)_2$. $^1H$ NMR (300 MHz, $CDCl_3$) δ: 0.02 (s, 9H, $Si(CH_3)_3$), 0.97 (s, 2H, $OCH_2CH_2Si$), 1.34 (s, 9H, $C(CH_3)_3$), 1.48 (s, 9H, $C(CH_3)_3$), 3.83 (s, 2H, $OCH_2CH_2Si$), 4.93 (s, 2H, $OCH_2O$), 6.95 (s, 2H, $OC_4H_2$), 7.34 (d, 2H, aryl-H), 7.65 (d, 2H, aryl-H). $^{13}C$ NMR (75 MHz, $CDCl_3$) δ: −1.2 ($Si(CH_3)_3$), 18.4 ($SiCH_2$), 31.2 ($C(CH_3)_3$), 31.6 ($C(CH_3)_3$), 34.8 ($C(CH_3)_3$), 35.7 ($C(CH_3)_3$), 67.7 ($OCH_2CH_2$), 97.0 ($OCH_2O$), 111.3, 123.4, 124.4, 124.8, 143.1, 146.0, 150.3, 150.7 (aryl).

3-$(MOM)_2$. $^1H$ NMR (300 MHz, $CDCl_3$) δ: 1.35 (s, 18H, $C(CH_3)_3$), 1.50 (s, 18H, $C(CH_3)_3$), 3.51 (s, 6H, $OCH_3$), 4.80 (s, 4H, $OCH_2O$), 7.28 (s, 2H, $SC_4H_2$), 7.31 (d, 2H, aryl-H), 7.38 (d, 2H, aryl-H). $^{13}C$ NMR (75 MHz, $CDCl_3$) δ: 31.1 ($C(CH_3)_3$), 31.7 ($C(CH_3)_3$), 34.8 ($C(CH_3)_3$), 35.7 ($C(CH_3)_3$), 57.7 ($OCH_3$), 98.5 ($OCH_2O$), 124.5, 126.5, 127.0, 128.2, 141.8, 143.0, 146.2, 151.1 (aryl).

4b-$(MOM)_2$. This compound was not isolated but used immediately in subsequent steps.

4c-$(MOM)_2$. $^1H$ NMR ($CDCl_3$) δ: 1.713 (s, 12H, Ad), 2.028 (s, 6H, Ad), 2.108 (s, 12H, Ad), 2.259 (s, 6H, $CH_3$), 3.267 (s, 6H, $OCH_3$), 4.474 (s, 4H, $OCH_2O$), 6.918 (s, 2H, Ar), 7.028 (s, 2H, Ar), 7.350 (t, 1H, Ph), 7.419 (d, 2H, Ph), 7.555 (s, 1H, Ph).

Deprotection of Bisphenols

Procedures analogous to those for 4a-$H_2$ were followed in accordance with the protecting group.

1a-H$_2$. $^1$H NMR (300 MHz, CDCl$_3$) δ: 1.39 (s, 18H, C(CH$_3$)$_3$), 1.48 (s, 18H, C(CH$_3$)$_3$), 7.46 (d, 2H, aryl-H), 7.51 (d, 2H, aryl-H), 7.67 (d, 2H, 3,5-NC$_5$H—H$_2$), 8.01 (t, 1H, 4-NC$_5$H$_2$—H), 10.59 (s, 2H, OH). $^{13}$C NMR (75 MHz, CDCl$_3$) δ: 29.8 (C(CH$_3$)$_3$), 31.8 (C(CH$_3$)$_3$), 34.6 (C(CH$_3$)$_3$), 35.6 (C(CH$_3$)$_3$), 120.5, 121.3, 123.0, 126.4, 137.5, 140.0, 141.5, 153.3, 157.6 (aryl). HRMS C$_{33}$H$_{45}$O$_2$N: Calcd mass: 487.3450. Measured mass: 487.3446. Yield 74% over two steps.

1b-H$_2$. $^1$H NMR (300 MHz, CDCl$_3$) δ: 0.71 (t, 9H, CH$_2$CH$_3$), 1.90 (q, 6H, CH$_2$CH$_3$), 2.35 (s, 3H, aryl-CH$_3$), 7.10 (d, 2H, aryl-H), 7.28 (d, 2H, aryl-H), 7.63 (d, 2H, NC$_5$H-3,5-H$_2$), 7.96 (t, 1H, NC$_5$H$_2$-4-H), 10.55 (br s, 2H, OH). $^{13}$C NMR (75 MHz, CDCl$_3$) δ: 8.8 (CH$_2$CH$_3$), 21.4 (aryl-CH$_3$), 26.2 (CH$_2$CH$_3$), 44.9 (aryl-C), 120.2, 121.6, 126.5, 127.7, 132.9, 134.4, 140.0, 153.4, 157.3 (aryl). HRMS C$_{33}$H$_{45}$O$_2$N: Calcd mass: 487.3450. Measured mass: 487.3460. Yield 54% over two steps.

1c-H$_2$. The crude product is suspended in acidified methanol and heated to reflux for 4 hours to remove both impurities and the protecting group. After cooling to room temperature, filtration of the suspension gives a pale yellow solid: 507 mg, 60%. $^1$H NMR (CD$_2$Cl$_2$) δ: 1.790 (s, 12H, Ad), 2.072 (s, 6H, Ad), 2.208 (s, 12H, Ad), 2.352 (s, 6H, CH$_3$), 7.143 (s, 2H, Ar), 7.330 (s, 2H, Ar) 7.672 (d, 2H, py), 8.008 (t, 1H, py), 10.501 (bs, 2H, OH).

2-H$_2$. Compound 2-(SEM)$_2$ (1.5 g, 2 mmol, 1 equiv) was dissolved in HMPA (50 mL) and a THF solution of (nBu)$_4$NF (1 M in THF with 5% water, 20.4 mL, 10 equiv). The color of the mixture gradually changed from colorless to orange to green. After two days of stirring at room temperature, water was added and an CH$_2$Cl$_2$ extraction was performed. Organic fractions were dried over MgSO$_4$ and filtered, and volatile materials were removed by rotary evaporation. Remaining HMPA was removed Kugelrohr distillation. Recrystallization from CH$_3$CN provides the desired product as a white powder (0.7645 g, 1.6 mmol, 80% yield). $^1$H NMR (500 MHz, CDCl$_3$) δ: 1.35 (s, 18H, C(CH$_3$)$_3$), 1.48 (s, 18H, C(CH$_3$)$_3$), 6.58 and 6.79 (s, 2H each, OH and OC$_4$H$_2$), 7.35 (d, 2H, aryl-H), 7.39 (d, 2H, aryl-H). $^{13}$C NMR (125 MHz, CDCl$_3$) δ: 29.9 (C(CH$_3$)$_3$), 31.7 (C(CH$_3$)$_3$), 34.6 (C(CH$_3$)$_3$), 35.4 (C(CH$_3$)$_3$), 109.1, 116.6, 122.0, 125.0, 136.8, 142.7, 149.6, 152.1 (aryl). HRMS C$_{32}$H$_{44}$O$_3$: Calcd mass: 476.3290. Measured mass: 476.3314.

3-H$_2$. $^1$H NMR (300 MHz, C$_6$D$_6$) δ: 1.30 (s, 18H, C(CH$_3$)$_3$), 1.61 (s, 18H, C(CH$_3$)$_3$), 5.57 (s, 2H, OH). 6.72 (s, 2H, SC$_4$H$_2$), 7.41 (d, 2H, aryl-H), 7.54 (d, 2H, aryl-H). $^{13}$C NMR (75 MHz, CDCl$_3$) δ: 29.9 (C(CH$_3$)$_3$), 31.8 (C(CH$_3$)$_3$), 34.6 (C(CH$_3$)$_3$), 35.4 (C(CH$_3$)$_3$), 120.4, 125.0, 125.4, 127.3, 136.0 (aryl). HRMS C$_{32}$H$_{44}$O$_2$S: Calcd mass: 492.3062. Measured mass: 492.3067. Yield 69% over two steps.

4b-H$_2$. The crude product is suspended in acidified methanol and heated to reflux for 4 hours to remove both impurities and the protecting group. After cooling to room temperature, removal of solvent gives an off-white crystalline solid: 2.9 g, 12%. $^1$H NMR (CDCl$_3$) δ: 1.442 (s, 18H, t-Bu), 2.320 (s, 6H, CH$_3$), 5.297 (s, 2H, OH), 6.936 (d, 2H, Ar), 7.118 (d, 2H, Ar), 7.494 (dd, 2H, Ph), 7.553 (bs, 1H, Ph), 7.608 (t, 1H, Ph).

4c-H$_2$. The crude product is suspended in acidified methanol and heated to reflux for two days to remove both impurities and the protecting group. After cooling to room temperature, filtration of the suspension gives a tan solid: 13.2 g, 36%. $^1$H NMR (CDCl$_3$) δ: 1.790 (s, 12H, Ad), 2.094 (s, 6H, Ad), 2.182 (s, 12H, Ad), 2.327 (s, 6H, CH$_3$), 5.290 (s, 2H, OH), 6.935 (s, 2H, Ar), 7.074 (s, 2H, Ar), 7.502 (d, 2H, Ph), 7.541 (s, 1H, Ph), 7.597 (t, 1H, Ph).

Example 2

Figure 3B:
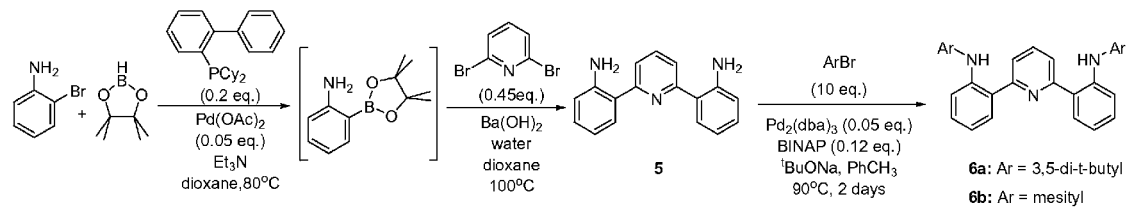
FIG. 3B. shows a schematic illustration of an exemplary reaction scheme (scheme 2) for the preparation of a semi-rigid tridentate ligand framework of organometallic complexes according to an embodiment herein described.

Preparation of Bisanilide Ligands (Scheme 2 FIG. 3b)

Exemplary bisanilide ligands were prepared according to a procedure schematically illustrate in Scheme 2 (FIG. 2B)

Synthesis of 2,6-bis(aniline)pyridine (5)

A 200 mL flask was charged with 2-bromoaniline (2.522 g, 14.66 mmol), palladium (II) acetate (166.8 mg, 743 µmol), [1,1'-biphenyl]-3-yldicyclohexyl phosphine (989 mg, 2.822 mmol), triethyl amine (8 mL, 57.55 mmol) and dioxane (30 mL). Pinalcolborane (6.3 mL, 43.41 mmol) was added slowly which led to gas evolution and coloring the solution to dark green. After stirring for 2.5 h at 80° C., the mixture was cooled to room temperature. Under an argon flow, solid Ba(OH)$_2$.8H$_2$O (14 g), a solution of 2,6-dibomopyridine (1.548 g, 6.534 mmol) in dioxane (10 mL) and deoxygenated water (7 mL) were added sequentially by syringes. The mixture was stirred vigorously at 100° C. for another 20 h before bringing it to room temperature and quenching it with 50 mL of water. The solid was removed by filtration, and the volatile substances were partially removed. Separation was performed with dichloromethane and water. Upon removal of the volatiles from the organic extract, brown oil was obtained. This was passed though a silica gel column using mixtures of dichloromethane and ethylacetate that ranged from 20:1 to 7:1. The fractions containing the desired product were collected and left under high vacuum, in a Kugelrohr distillation apparatus at 90° C. Pure compound 2,6-bis(aniline)pyridine was obtained as a pale brown solid in 75% yield (1.3 g). $^1$H NMR (CDCl$_3$) δ: 5.34 (bs, 4H, NH$_2$), 6.77 (dd, 2H), 6.84 (td, 2H), 7.22 (td, 2H), 7.53 (d, 2H, Py-H), 7.56 (dd, 2H), 7.85 (t, 1H, Py-H). $^{13}$C NMR (CDCl$_3$) δ: 117.1, 117.8, 120.2, 123.0, 129.9, 130.0, 138.1, 146.1, 157.7.

Synthesis of 2,6-bis(N-3,5-di-t-butylaniline)pyridine (6a)

2,6-Bis(aniline)pyridine (500 mg, 1.914 mmol), 3,5-di-t-butyl-bromobenzene (1.26 g, 4.688 mmol), Pd$_2$(dba)$_3$ (87.6 mg, 95.7 µmol), BINAP (128.7 mg, 229.5 µmol) and sodium t-butoxide (552 mg, 5.744 mmol) were dissolved in 15 mL of toluene. The mixture was stirred for 48 h at 90° C. before cooling it to room temperature and quenching the reaction with 20 mL of water. After separation with dichloromethane, the volatiles were removed in vacuo from the organic extract. The obtained orange oil was passed through a silica gel column by a 20:1 mixture of dichloromethane and ethyl acetate and then was triturated from cold methanol and collected by filtration. 854 mg of pale-yellow solid 6a were obtained after a single wash (70% yield). $^1$H NMR (CDCl$_3$) δ: 1.22 (s, 36H, C(CH$_3$)$_3$), 6.93 (td, 2H), 6.99 (t, 2H tBu-Ph-H), 7.05 (d, 4H, tBu-Ph-H), 7.30 (td, 2H), 7.54 (dd, 2H), 7.66 (d, 4H, Ph-H, Py-H), 7.90 (t, 1H, Py-H), 9.8 (s, 2H, NH). $^1$H-NMR (C$_6$D$_6$) δ: 1.22 (s, 36H, C(CH$_3$)$_3$), 6.86 (td, 2H, Ph-H), 7.14 (t, 2H), 7.1-7.2 (d+t, 3H, Py-H), 7.24 (td, 2H, Ph-H), 7.32 (d, 4H), 7.52 (dd, 2H, Ph-H), 7.85 (dd, 2H, Ph-H), 10.14 (s, 2H, NH). $^{13}$C NMR (CDCl$_3$) δ: 31.6 (CH$_3$), 35.0 (C(CH$_3$)$_3$), 114.6, 115.8, 116.1, 118.9, 120.5, 124.7, 130.0, 130.5, 138.5, 141.5, 143.2, 151.9, 157.3.

Synthesis of 2,6-bis(N-mesitylaniline)pyridine (6b)

This compound was prepared in a similar fashion to the other substituted bisaniline to give an off-white solid: 460 mg, 74%. $^1$H NMR (CDCl$_3$) δ: 2.11 (s, 12H, o-CH$_3$), 2.36 (s, 6H, p-CH$_3$), 6.38 (dd, 2H), 6.85 (td, 2H), 6.94 (s, 4H, Ms-H), 7.19 (td, 2H), 7.67 (dd, 2H), 7.74 (d, 2H, Py-H), 7.97 (t, 1H, Py-H), 8.27 (s, 2, NH). $^1$H-NMR (C$_6$D$_6$) δ: 2.01 (s, 12H, o-CH$_3$), 2.15 (s, 6H, p-CH$_3$), 6.50 (dd, 2H), 6.74 (s, 4H, Ms-H; td, 2H), 7.02 (td, 2H), 7.2-7.4 (m, 3H, Py-H), 7.55 (dd, 2H), 8.52 (s, 2H, NH). $^{13}$C NMR (CDCl$_3$) δ: 18.6 (CH$_3$), 21.1 (CH$_0$), 113.3, 117.2, 120.9, 123.2, 129.1, 130.0, 130.1, 135.2, 136.1, 136.2, 137.9, 145.5, 158.2.

Example 3

Preparation of Metal Complexes

Preparation of Group 4 Complexes

Studies with group 4 metals utilized precursors for alcohol elimination, salt metathesis, and alkane elimination. The ligand (1c-H$_2$) was treated with Ti(OiPr)$_4$ which, upon heating at 80° C. overnight gave the desired product. Another successful route was through salt metathesis with TiCl$_4$(THF)$_2$. This reaction entailed deprotonating 1c-H$_2$ with potassium benzyl then removing the KCl by filtration to give 1c-TiCl$_2$(THF).

Titanium, zirconium, and hafnium dibenzyl complexes have been prepared by toluene elimination between the tetrabenzyl precursors and bisphenols (Scheme 3 FIG. 2C). These reactions have been performed in diethyl ether. The titanium complexes are obtained as red (1c-TiBn$_2$, 2-TiBn$_2$, 3-TiBn$_2$, and 4b-TiBn$_2$) or orange (1a-TiBn$_2$ and 1b-TiBn$_2$) solids. The zirconium complexes are yellow (1a-ZrBn$_2$, 1b-ZrBn$_2$, 1c-ZrBn$_2$ and 3-ZrBn$_2$) or colorless (2-ZrBn$_2$) solids. The hafnium complexes are white (4b-HfBn$_2$ and 4cHfBn$_2$) solids. Coordinated ether was not observed by NMR spectroscopy for titanium and zirconium complexes indicating that the precatalysts are five-coordinate. However, for the hafnium complexes, NMR data show a single coordinated ether molecule indicating that those complexes are six-coordinate. $^1$H NMR spectra of all dibenzyl complexes except 4b-TiBn$_2$ show a singlet for the benzyl CH$_2$ protons. A variable temperature $^1$H NMR study was performed for 1a-TiBn$_2$. The benzyl peak was found to remain a sharp singlet at temperatures as low as −80° C. indicating fast exchange between different geometries.

The solution symmetry of the present species and their ability to exchange between different geometries may be important with regard to controlling polymer microstructure. For instance, a C$_2$ structure may enforce isotactic polymerization if the steric transfer to the metal site is efficient enough, while the above C$_s$ and C$_{2v}$ structures should give atactic polymers. If C$_2$/C$_s$ inter-conversion occurs at a rate slower than the insertion rates, stereoblock polymers could be obtained if enantiomorphic site control is operative. A similar type of oscillation of the catalyst has been proposed to lead to isotactic-atactic stereoblock polymers. (Coates, G. W.; Waymouth, R. M. *Science* 1995, 267, 217-219.) In a related process, inversion between the two C$_2$ structures could be controlled by the polymer chain end. In this case, syndiotactic polymer could be generated if the inversion occurs after each insertion. (Tian, J.; Hustad, P. D.; Coates, G. W. *J. Am. Chem. Soc.* 2001, 123, 5134-5135. Milano, G.; Cavallo, L.; Guerra, G. J. *Am. Chem. Soc.* 2002, 124, 13368-13369.)

Preparation of the Vanadium Complex

To study the difference between group 4 and 5 metals, a vanadium complex was synthesized. A salt metathesis route was employed to generate 1c-VCl(THF)$_2$ using the trivalent precursor VCl$_3$(THF)$_3$. The resulting orange/brown solid is paramagnetic and shows very broad peaks in the $^1$H NMR spectrum. The solution magnetic susceptibility was determined using the Evans Method to give a $\mu_{eff}$=2.89 $\mu_B$. (Evans, D. F. *J. Chem. Soc.* 1959, 2003-2005.) This matches the predicted value ($\mu_{eff}$(theoretical)=2.82) for two unpaired electrons in trivalent vanadium complexes. Elemental analysis supports the assigned structure.

Figure 3C:
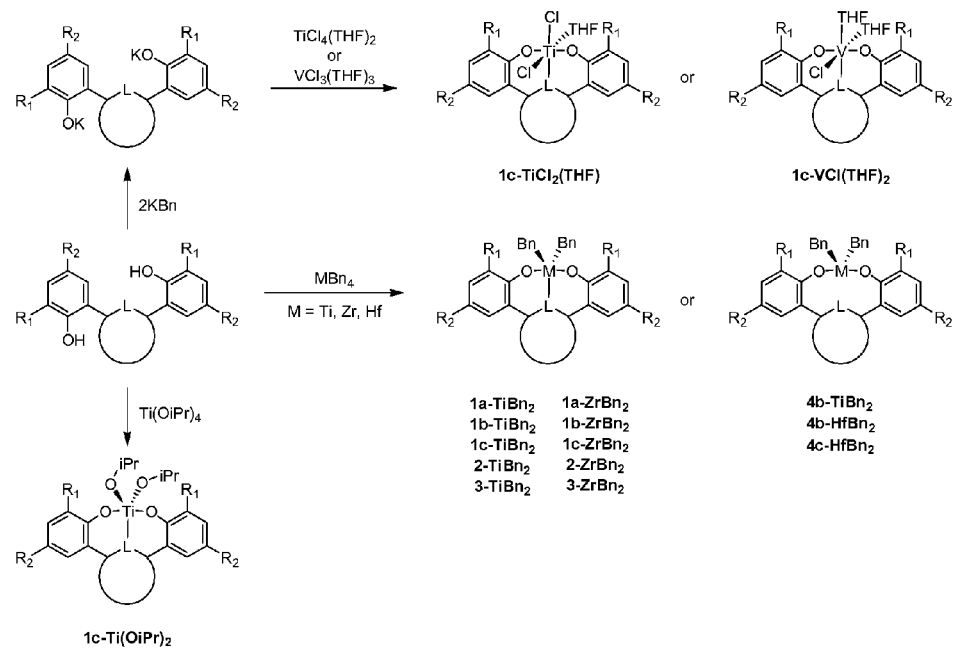
FIG. 3C. shows a schematic illustration of an exemplary reaction scheme (scheme 3) for the preparation of organometallic complexes according to an embodiment herein described.

General Procedure for the Preparation of Group 4 Dibenzyl Complexes (see Scheme 3 FIG. 3C)

An Et$_2$O (10 mL) solution of phenol 1a-H$_2$ (100 mg, 0.206 mmol) was added to a solution of TiBn$_4$ (86 mg, 0.206 mmol) in Et$_2$O (5 mL). The mixture was stirred at room temperature for 5-12 h. Volatile materials were removed under vacuum and the residue was mixed with petroleum ether and recrystallized at −35° C. The desired product was collected by filtration and washed with cold petroleum ether. This procedure gives 130 mg (0.181 mmol, 87%) of 1a-TiBn$_2$ as an orange powder. $^1$H NMR (500 MHz, CD$_2$Cl$_2$) δ: 1.41 (s, 18H, C(CH$_3$)$_3$), 1.94 (s, 18H, C(CH$_3$)$_3$), 3.48 (s, 4H, TiCH$_2$), 6.29-6.37 (m, 6H, m- and p-C$_6$H$_2$—H$_3$), 6.43 (d, 4H, o-C$_6$H$_3$—H$_2$), 7.16 (d, 2H, aryl-H), 7.43 (d, 2H, 3,5-NC$_5$H—H$_2$), 7.65 (t, 1H, 4-NC$_5$H$_2$—H), 7.68 (d, 2H, aryl-H). No diastereotopic hydrogens are observed at −80° C. as benzyl protons are a singlet. $^{13}$C NMR (125 MHz, CD$_2$Cl$_2$) δ: 31.5 (C(CH$_3$)$_3$), 32.0 (C(CH$_3$)$_3$), 35.0 (C(CH$_3$)$_3$), 36.2 (C(CH$_3$)$_3$), 84.5 (TiCH$_2$), 122.8, 123.9, 126.1, 127.0, 127.2, 127.8, 129.4, 136.0, 138.3, 138.5, 141.7, 156.5, 157.3 (aryl). Anal. calcd. for C$_{47}$H$_{57}$NO$_2$Ti (%): C, 78.86; H, 8.03; N, 1.96. Found: C, 77.62; H, 8.38; N, 1.95.

1b-TiBn$_2$. $^1$H NMR (500 MHz, C$_6$D$_6$) δ: 1.03 (t, 18H, CH$_2$CH$_3$), 2.34 (s, 6H, aryl-CH$_3$), 2.58 (q, 12H, CH$_2$CH$_3$), 3.83 (s, 4H, TiCH$_2$), 6.32 (t, 2H, p-C$_6$H$_3$—H$_2$), 6.51 (t, 4H, m-C$_6$H$_3$—H$_2$), 6.71 (t, 1H, 4-NC$_5$H$_2$—H), 6.77 (d, 4H, o-C$_6$H$_3$—H$_2$), 6.91 (d, 2H, 3,5-NC$_5$H—H$_2$), 6.93 (d, 2H, aryl-H), 7.43 (d, 2H, aryl-H). $^{13}$C NMR (125 MHz, C$_6$D$_6$) δ: 9.4 (CH$_2$CH$_3$), 21.8 (aryl-CH$_3$), 27.3 (CH$_2$CH$_3$), 44.9 (aryl-C), 84.6 (TiCH$_2$), 123.2, 124.0, 127.9, 128.1, 128.6, 130.0, 130.2, 133.4, 133.8, 137.6, 138.8, 157.2, 157.5 (aryl). Anal. calcd. for C$_{47}$H$_{57}$NO$_2$Ti (%): C, 78.86; H, 8.03; N, 1.96. Found: C, 78.53; H, 8.25; N, 2.10. 78% yield.

1c-TiBn$_2$. $^1$H NMR (C$_6$D$_6$) δ: 1.945 (dd, 12H, Ad, J$_{HH}$=12.5 Hz, J$_{HH}$=77.5 Hz), 2.249 (s, 6H, Ad), 2.332 (s, 6H, CH$_3$), 2.874, (s, 12H, Ad), 4.053 (s, 4H, CH$_2$), 6.304 (t, 2H, Ph), 6.466 (t, 4H, Ph), 6.721 (t, 1H, py), 6.865 (d, 2H, py), 6.870 (d, 4H, Ph), 6.886 (s, 2H, Ar), 7.381 (s, 2H, Ar). Analysis: Calculated (Found) C, 80.79 (80.57); H, 7.29 (7.18); N, 1.78 (1.76). 75% yield.

2-TiBn$_2$. $^1$H NMR (500 MHz, C$_6$D$_6$) δ: 1.37 (s, 18H, C(CH$_3$)$_3$), 2.12 (s, 18H, C(CH$_3$)$_3$), 3.89 (s, 4H, TiCH$_2$), 6.37 (t, 2H, p-C$_6$H$_3$—H$_2$), 6.51-6.54 (m, 6H, overlap m-C$_6$H$_3$—H$_2$ and OC$_4$—H$_2$), 6.99 (d, 4H, o-C$_6$H$_3$—H$_2$), 7.49 (d, 2H, aryl-H), 7.73 (d, 2H, aryl-H). $^{13}$C NMR (125 MHz, C$_6$D$_6$) δ: 32.0 (C(CH$_3$)$_3$), 32.1 (C(CH$_3$)$_3$), 35.0 (C(CH$_3$)$_3$), 36.6 (C(CH$_3$)$_3$), 88.2 (TaCH$_2$), 108.7, 121.3, 122.1, 124.1, 124.5, 128.4, 130.6, 137.9, 138.0, 143.1, 154.2, 155.7 (aryl). $^{13}$C NMR (125 MHz, CDCl$_3$) δ: 31.5 (C(CH$_3$)$_3$), 31.9 (C(CH$_3$)$_3$), 34.8 (C(CH$_3$)$_3$), 36.1 (C(CH$_3$)$_3$), 87.4 (TiCH$_2$), 108.2, 120.7, 121.3, 123.3, 123.9, 127.9, 129.6, 137.2, 137.7, 142.7, 153.5, 155.0 (aryl). 62% yield.

3-TiBn$_2$. $^1$H NMR (500 MHz, C$_6$D$_6$) δ: 1.33 (s, 18H, C(CH$_3$)$_3$), 2.06 (s, 18H, C(CH$_3$)$_3$), 3.93 (s, 4H, TiCH$_2$), 6.23 (s, 2H, SC$_4$H$_2$), 6.56 (t, 2H, p-C$_6$H$_3$—H$_2$), 6.3-6.5 (v br s, 4H, m-C$_6$H$_3$—H$_2$ or o-C$_6$H$_3$—H$_2$), 6.6-7.2 (v br s, 4H, m-C$_6$H$_3$—

H$_2$ or o-C$_6$H$_3$—H$_2$), 7.41 (d, 2H, aryl-H), 7.74 (d, 2H, aryl-H). $^1$H NMR (500 MHz, CD$_2$Cl$_2$) δ: 1.38 (s, 18H, C(CH$_3$)$_3$), 1.95 (s, 18H, C(CH$_3$)$_3$), 3.58 (br s, 4H, TiCH$_2$), 6.30 (s, 2H, SC$_4$H$_2$), 6.4-7.0 (br, 10H, C$_6$H$_5$), 7.27 (d, 2H, aryl-H), 7.56 (d, 2H, aryl-H). $^{13}$C NMR (125 MHz, CD$_2$Cl$_2$) δ: 31.9 (C(CH$_3$)$_3$), 32.0 (C(CH$_3$)$_3$), 34.9 (C(CH$_3$)$_3$), 36.6 (C(CH$_3$)$_3$), 88.4 (TiCH$_2$), 122.9, 124.0, 125.7, 126.3, 127.2, 128.7, 131.2, 135.5, 137.7, 139.9, 142.9, 160.5 (aryl).

4b-TiBn$_2$. $^1$H NMR (C$_6$D$_6$) δ: 1.603 (s, 18H, C(CH$_3$)$_3$), 1.967 (s, 2H, CH$_2$), 2.205 (s, 6H, CH$_3$), 3.441 (s, 2H, CH$_2$), 6.593 (d, 2H, Ph), 6.631 (s, 1H, Ph), 6.702 (t, 1H, Ph), 6.836 (t, 2H, Bn), 6.994-7.071 (br, 10H, Bn and Ar), 7.223 (d, 2H, Ar).

1a-ZrBn$_2$. $^1$H NMR (500 MHz, C$_6$D$_6$) δ: 1.39 (s, 18H, C(CH$_3$)$_3$), 1.79 (s, 18H, C(CH$_3$)$_3$), 2.70 (s, 4H, ZrCH$_2$), 6.63 (t, 2H, p-C$_6$H$_3$—H$_2$), 6.78 (t, 4H, m-C$_6$H$_3$—H$_2$), 6.83 (t, 1H, 4-NC$_5$H$_2$—H), 7.02 (d, 4H, o-C$_6$H$_3$—H$_2$), 7.06 (d, 2H, 3,5-NC$_5$H—H$_2$), 7.10 (d, 2H, aryl-H), 7.70 (d, 2H, aryl-H). $^{13}$C NMR (125 MHz, C$_6$D$_6$) δ: 31.1 (C(CH$_3$)$_3$), 32.3 (C(CH$_3$)$_3$), 34.9 (C(CH$_3$)$_3$), 36.0 (C(CH$_3$)$_3$), 60.1 (ZrCH$_2$), 123.3, 124.8, 126.4, 127.5, 129.7, 130.1, 136.3, 139.0, 139.1, 141.7, 155.1, 160.5 (aryl). 88% yield.

1b-ZrBn$_2$. $^1$H NMR (500 MHz, C$_6$D$_6$) δ: 0.92 (t, 18H, CH$_2$CH$_3$), 2.29 (s, 6H, aryl-CH$_3$), 2.33 (q, 12H, CH$_2$CH$_3$), 2.83 (s, 4H, ZrCH$_2$), 6.53 (t, 2H, p-C$_6$H$_3$—H$_2$), 6.72 (t, 4H, m-C$_6$H$_3$—H$_2$), 6.79 (d, 2H, aryl-H), 6.83 (app t, 1H, 4-NC$_5$H$_2$—H), 6.94 (d, 2H, 3,5-NC$_5$H—H$_2$), 6.97 (d, 4H, o-C$_6$H$_3$—H$_2$), 7.29 (d, 2H, aryl-H). $^{13}$C NMR (125 MHz, C$_6$D$_6$) δ: 9.3 (CH$_2$CH$_3$), 15.7, 21.6 (aryl-CH$_3$), 26.9 (CH$_2$CH$_3$), 45.4 (aryl-C), 61.2, 66.1, 123.1, 125.3, 127.9, 129.0, 129.7, 129.9, 131.0, 133.3, 133.5, 138.8, 138.9, 155.1, 160.0 (aryl). 58% yield.

1c-ZrBn$_2$. $^1$H NMR (C$_6$D$_6$) δ: 1.909 (dd, 12H, Ad), 2.205 (s, 6H, Ad), 2.271 (s, 6H, CH$_3$), 2.608, (s, 12H, Ad), 3.413 (s, 4H, CH$_2$), 6.258 (t, 2H, Ph), 6.445 (t, 4H, Ph), 6.700 (d, 2H, py), 6.843 (t, 1H, py), 6.973 (d, 4H, Ph), 7.116 (s, 2H, Ar), 7.244 (s, 2H, Ar). 40% yield.

2-ZrBn$_2$. $^1$H NMR (500 MHz, C$_6$D$_6$) δ: 1.38 (s, 18H, C(CH$_3$)$_3$), 1.76 (s, 18H, C(CH$_3$)$_3$), 2.51 (s, 4H, ZrCH$_2$), 6.53 (s, 2H, OC$_4$H$_2$), 6.67 (t, 2H, p-C$_6$H$_3$—H$_2$), 6.82 (t, 4H, m-C$_6$H$_3$—H$_2$), 7.03 (d, 4H, o-C$_6$H$_3$—H$_2$), 7.48 (d, 2H, aryl-H), 7.59 (d, 2H, aryl-H). $^{13}$C NMR (125 MHz, C$_6$D$_6$) δ: 31.0 (C(CH$_3$)$_3$), 32.1 (C(CH$_3$)$_3$), 34.9 (C(CH$_3$)$_3$), 36.1 (C(CH$_3$)$_3$), 61.4 (ZrCH$_2$), 109.7, 121.4, 122.3, 124.1, 124.7, 129.6, 130.4, 137.5, 142.6, 152.9, 156.2 (aryl). 69% yield.

3-ZrBn$_2$. $^1$H NMR (500 MHz, CD$_2$Cl$_2$) δ: 1.35 (s, 18H, C(CH$_3$)$_3$), 1.63 (s, 18H, C(CH$_3$)$_3$), 2.28 (br s, 4H, ZrCH$_2$), 6.51 (s, 2H, SC$_4$H$_2$), 6.68 (br s, 4H, o-C$_6$H$_3$—H$_2$), 6.85 (br t, 4H, m-C$_6$H$_3$—H$_2$), 6.99 (t, 1H, p-C$_6$H$_4$—H), 7.29 (d, 2H, aryl-H), 7.42 (d, xH, aryl-H). $^{13}$C NMR (125 MHz, CD$_2$Cl$_2$) δ: 31.0 (C(CH$_3$)$_3$), 31.8 (C(CH$_3$)$_3$), 34.8 (C(CH$_3$)$_3$), 36.2 (C(CH$_3$)$_3$), 62.7 (ZrCH$_2$), 123.2, 123.9, 124.6, 125.5, 128.0, 130.0, 130.3, 137.5, 138.5, 142.4, 158.0 (aryl). 58% yield.

4b-HfBn$_2$. $^1$H NMR (C$_6$D$_6$) δ: 0.546 (t, 6H, OCH$_2$CH$_3$), 2.235 (s, 6H, CH$_3$), 2.785 (s, 4H, CH$_2$), 3.007 (q, 4H, OCH$_2$CH$_3$), 6.131 (s, 1H, Ph), 6.562 (t, 1H, Ph), 6.802-7.094 (br, 14H, Ph and Bn), 7.289 (d, 2H, Ar).

4c-HfBn$_2$. $^1$H NMR (C$_6$D$_6$) δ: 0.862 (t, 6H, OCH$_2$CH$_3$), 1.828 (dd, 12H, Ad), 2.248 (s, 6H, Ad), 2.283 (s, 6H, CH$_3$), 2.829 (s, 4H, CH$_2$), 3.120 (q, 4H, OCH$_2$CH$_3$), 5.758 (s, 1H, Ph), 6.562 (t, 1H, Ph), 6.683-7.120 (br, 14H, Ph and Bn), 7.268 (d, 2H, Ar).

General procedure for the synthesis of transition metal chloride complexes (1c-TiCl$_2$(THF)). Benzyl potassium (47 mg, 0.35 mmol) and pyridine-2,6-bis(2-adamantyl-4-methylphenol) (1c-H$_2$, 100 mg, 0.178 mmol) are dissolved in THF (15 mL) and stirred for 30 minutes. This solution is added to TiCl$_4$(THF)$_2$ (60 mg, 0.178 mmol) and stirred for 30 minutes. The THF is removed in vacuo. The resulting solid is suspended in diethyl ether and filtered. The filtrate is dried under vacuum to give a dark red crystalline solid: 77 mg, 58%. $^1$H NMR (C$_6$D$_6$) δ: 0.813 (m, 4H, THF), 2.008 (dd, 18H, Ad), 2.245 (s, 6H, CH$_3$), 2.612, (s, 12H, Ad), 3.399 (m, 4H, THF), 6.895 (d, 2H, py), 7.000 (t, 1H, py), 7.156 (s, 2H, Ar), 7.276 (s, 2H, Ar). Analysis: Calculated (Found) C, 69.05 (68.44); H, 6.74 (7.14); N, 1.87 (1.93); Ti: 6.40 (5.94).

1c-VCl(THF)$_2$. The complex is prepared analogously to complex 1c-TiCl$_2$(THF) to give an orange/brown solid: 166 mg, 59%. $^1$H NMR (C$_6$D$_6$): paramagnetic. Analysis: Calculated (Found) C, 71.37 (72.04); H, 6.92 (7.53); N, 1.85 (1.70); Cl: 4.68 (4.6).

Synthesis of titanium di-iso-propoxide (1c-Ti(O$^i$Pr)$_2$)

Titanium tetra-iso-propoxide (100 mg, 0.35 mmol) was dissolved in benzene (10 mL). Pyridine-2,6-bis(2-adamantyl-4-methylphenol) (1c-H$_2$, 200 mg, 0.35 mmol) predissolved in benzene (10 mL) was added to the titanium. The reaction was heated overnight at 80° C. After cooling, the solvent was removed in vacuo to give a yellow solid: 142 mg, 56%. $^1$H NMR (C$_6$D$_6$) δ: 1.09 (d, 12H, i-Pr), 1.90 (dd, 12H, Ad), 2.19 (s, 6H, Ad), 2.31 (s, 6H, CH$_3$), 2.52, (s, 12H, Ad), 5.02 (m, 2H, CH), 7.04 (t, 1H, py), 7.06 (d, 2H, py), 7.14 (d, 4H, Ph), 7.17 (s, 2H, Ar), 7.31 (s, 2H, Ar).

Figure 3D:
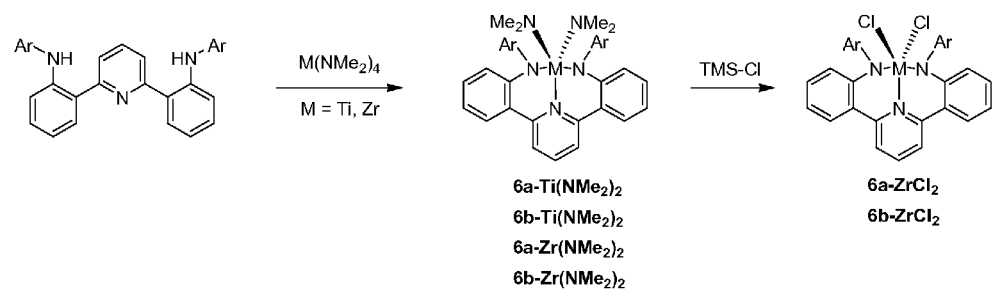
FIG. 3D shows a schematic illustration of an exemplary reaction scheme (scheme 4) or the preparation of organometallic complexes according to an embodiment herein described
Figure 4A:
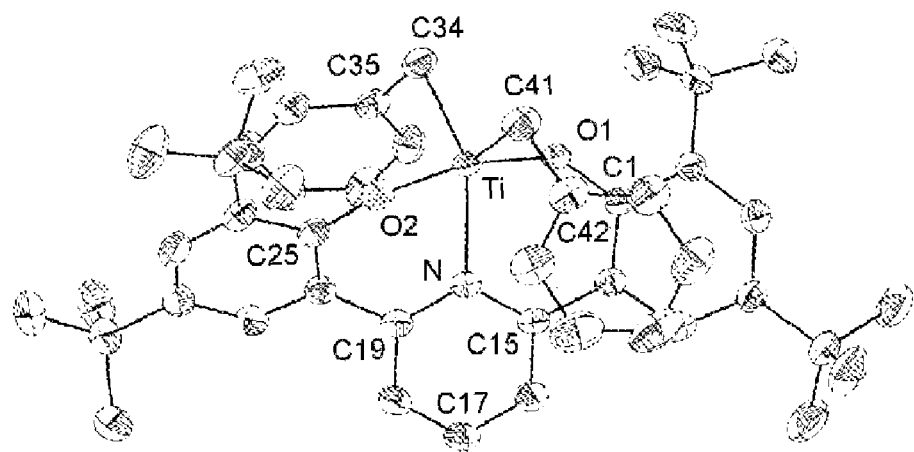
FIGS. 4A and 4B shows a schematic illustration of the structure of an exemplary organometallic complex according to an embodiment herein described. View A is roughly perpendicular to the Ti—N vector and view B is along the Ti—N vector.
Figure 4B:
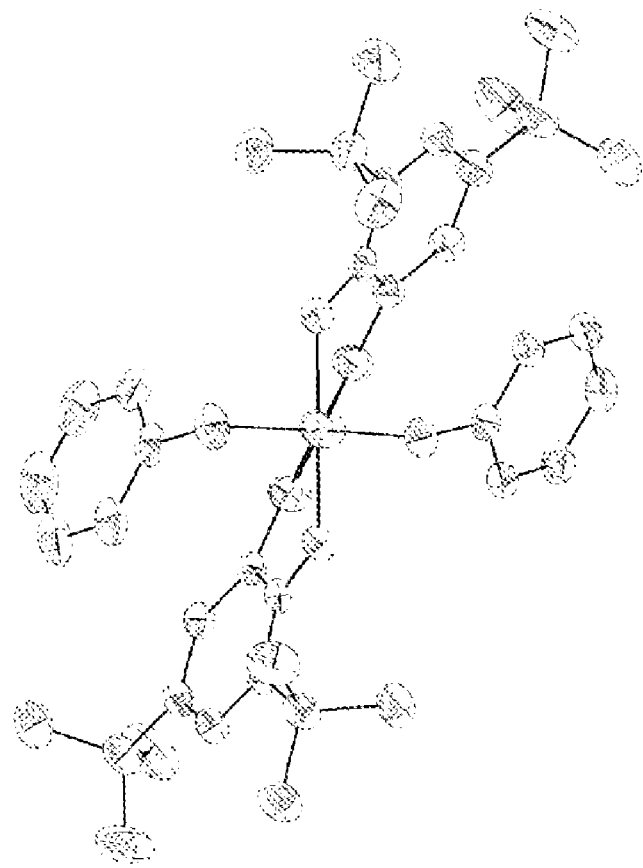
Figure 5A:
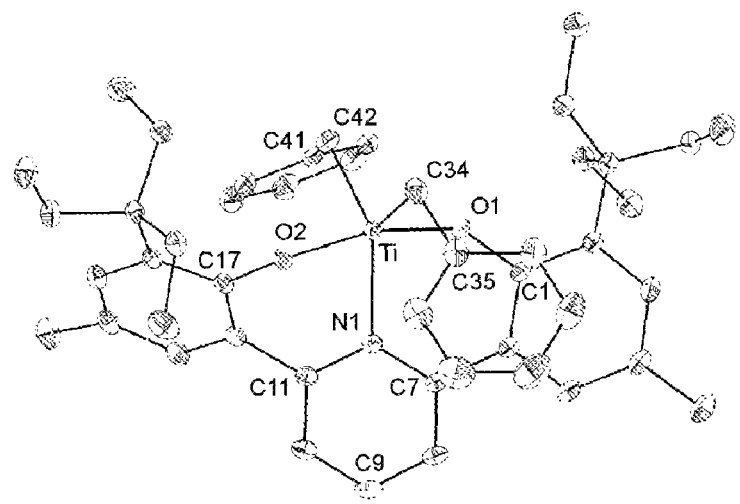
FIGS. 5A and 5B shows a schematic illustration of the structure of an exemplary organometallic complex according to an embodiment herein described. View A is roughly perpendicular to the Ti—N vector and view B is along the Ti—N vector.
Figure 5B:
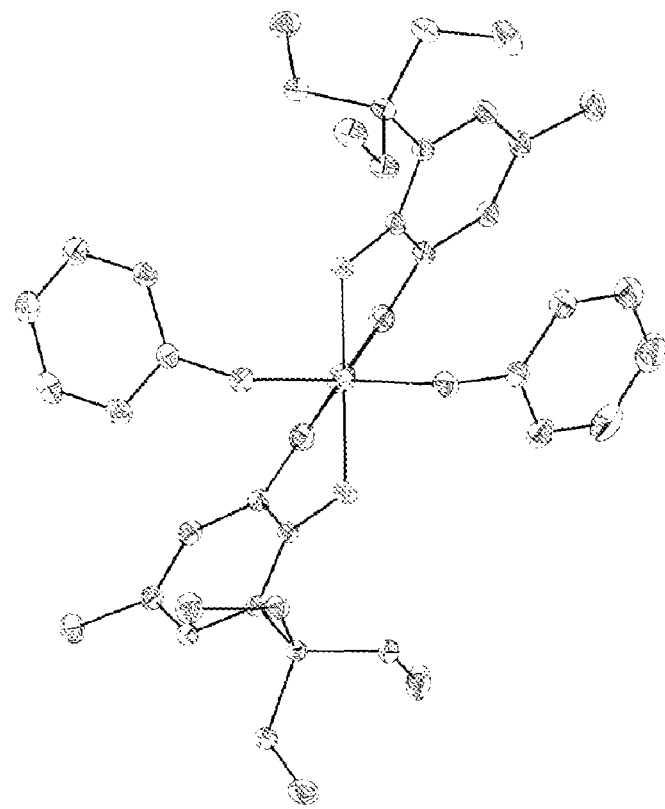
Figure 6:
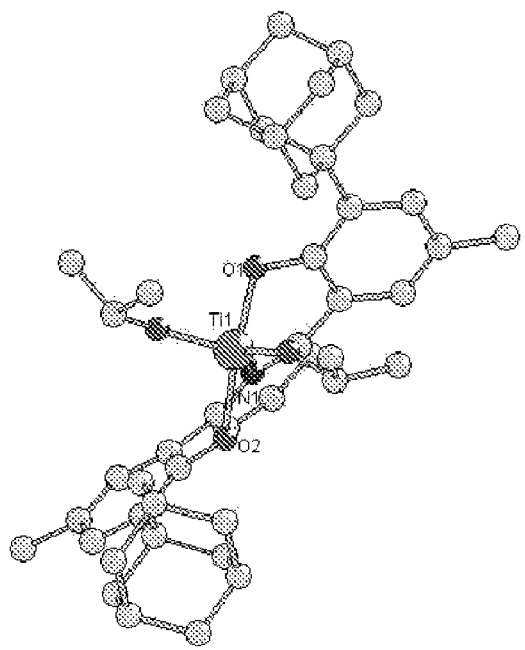
FIG. 6 shows a schematic illustration of the structure of an exemplary organometallic complex according to an embodiment herein described, wherein the hydrogen atoms have been omitted for clarity.

Synthesis of Group 4 bis(dimethylamide) Complexes (Scheme 4 FIG. 3D)

6a-Ti(NMe$_2$)$_2$. A 100 mL Schlenk flask was charged with titanium tetrakis-dimethylamide (13.3 mg, 59.3 µmol), 6a (37.2 mg, 58.3 µmol) and toluene. The solution was stirred for two days at 60° C. before cooling to room temperature and removing the volatiles in vacuo. The solid was dissolved in diethyl ether and then the solution was left under vacuum to generate the desired product as a red solid. Recrystallization was performed by dissolving the solid in petroleum ether and a few drops of THF. $^1$H NMR (C$_6$D$_6$) δ: 1.24 (s, 36H, CCH$_3$), 3.17 (s, NCH$_3$), 6.7-6.9 (m, 7H), 6.95 (t, 2H), 7.01 (d, 2H), 7.22 (t, 2H), 7.30 (d, 2H), 7.41 (d, 2H).

6b-Ti(NMe$_2$)$_2$. A solution of bisaniline 6b (169.8 mg, 341 µmol) in 6 mL toluene at –35° C. was added to a cooled suspension of KBn (88.6 mg, 642 µmol) in 4 mL toluene. The reaction mixture was allowed to warm to room temperature. After 30 minutes, the red solid on the bottom had disappeared, and instead, an orange suspension was obtained. After 4 hours, the suspension was cooled to –35° C. again, and a cooled solution of TiCl$_2$(NMe$_2$)$_2$ (70.6 mg, 341 µmol) in 5 mL toluene was added dropwise. By the time the addition was done, the suspension disappeared, and the solution had become dark red. The solution was allowed to warm up to room temperature overnight, under stirring. The liquid was filtered through celite, and then the volatiles were removed to obtain the desired complex. $^1$H NMR (C$_6$D$_6$) δ: 1.98 (br. s, 12H, NCH$_3$), 2.19 (s, 6H, p-CH$_3$), 2.50, (s, 12H, o-CH$_3$), 6.57 (d, 2H), 6.71 (t, 2H), 6.83 (s, 4H), 7.09 (t, 2H), 7.1-7.2 (m, 1H), 7.28 (d, 2H), 7.62 (d, 2H) ppm. $^{13}$C-NMR (C$_6$D$_6$) δ: 19.5 (o-CH$_3$), 21.3 (p-CH$_3$), 44.4 (N—CH$_3$), 116.5, 116.6, 123.6, 123.6, 128.9, 129.2, 123.6, 131.1, 132.7, 134.8, 136.3, 151.4, 151.6, 154.6.

6a-Zr(NMe$_2$)$_2$. A procedure analogous to that for 6a-Ti(NMe$_2$)$_2$ was used. $^1$H NMR (C$_6$D$_6$) δ: 1.27 (s, 36H, CCH$_3$), 2.87 (s, 12H, NCH$_3$), 6.75 (t, 2H), 6.9-7.0 (m, 5H), 7.04 (s, 4H), 7.16 (t, 2H), 7.26 (d, 2H), 7.38 (d, 2H). $^{13}$C NMR (C$_6$D$_6$)

δ: 32.1 (CCH$_3$), 35.2 (CH$_0$), 41.3 (NCH$_3$), 113.9, 116.4, 120.6, 123.0, 126.7, 129.7, 130.9, 131.7, 138.9, 149.8, 151.6, 153.8, 154.9.

6b-Zr(NMe$_2$)$_2$. A procedure analogous to that for 6a-Ti (NMe$_2$)$_2$ was used. $^1$H NMR (C$_6$D$_6$) δ: 2.03 (br s, 12H, NCH$_3$), 2.21 (s, 6H, p-CH$_3$), 2.26 (s, 12H, o-CH$_3$), 6.67-6.75 (m, 5H), 6.86 (s, 4H), 7.1-7.2 (m, 6H), 7.55 (d, 2H). $^{13}$C NMR (C$_6$D$_6$) δ: 19.1 (CCH$_3$), 21.4 (CH$_0$), 39.5 (NCH$_3$), 116.6, 118.0, 122.6, 124.2, 129.3, 130.3, 132.0, 132.6, 134.9, 137.4, 149.0, 150.7, 154.8.55% yield.

Synthesis of Group 4 Dichloride Complexes
(Scheme 4 FIG. 3D)

6a-ZrCl$_2$. The solid bisamide 6a-Zr(NMe$_2$)$_2$ was dissolved in toluene (10 mL) and trimethylsilylchloride (32 μL, 253.4 μmol) was added via syringe. The mixture was heated to 55° C. and stirred for 16 hours. Volatiles were removed under vacuum, and the solid was redissolved in toluene and filtered through a glass filter. The solvent was removed under vacuum, and 91.7 mg of orange solid 6a-ZrCl$_2$ were obtained (100% yield). The complex was recrystallized from toluene as yellow crystals, or from diethyl ether as orange crystals of solvent-ligated 6a-ZrCl$_2$(OEt$_2$). $^1$H NMR (C$_6$D$_6$) δ: 1.18 (s, 36H, CH$_3$), 6.84 (t, 2H), 6.97-7.08 (m, 5H), 7.23-7.28 (m, 6H), 7.31 (s, 4H). $^{13}$C NMR (C$_6$D$_6$) δ: 32.0 (CH$_3$), 35.4 (CH$_0$), 119.3, 121.0, 123.5, 125.4, 127.6, 129.7, 131.2, 132.9, 140.1, 143.2, 149.7, 152.3, 154.7.

6b-ZrCl$_2$. Trimethylsilylchloride (9 μL, 63 μmol) was added via syringe to a solution of bisamide 6b-Zr(NMe$_2$)$_2$ (17.3 mg, 25.6 μmol) in 1 mL of benzene. The mixture was left at room temperature without any stirring. After 24 h the reaction was complete, and the solution was set aside for a few days at room temperature while yellow crystals of the complex formed. $^1$H NMR (C$_6$D$_6$) δ: 1.86 (s, 12H, o-CH$_3$), 2.13 (s, 6H, p-CH$_3$), 6.65-6.75 (m, 7H), 6.82 (t, 2H), 6.9-7.2 (m, 4H) 7.63 (dd, 2H). $^{13}$C NMR (C$_6$D$_6$) δ: 19.5, 20.8, 122.1, 122.3, 122.6, 123.5, 128.4, 129.3, 130.2, 130.9, 133.3, 137.2, 137.5, 138.8, 139.5, 143.3, 152.4.

Structural Characterization of Group 4 Dibenzyl
Complexes with Tridentate Bisphenolate Ligands Single-crystal X-ray diffraction studies have been instrumental in determining the binding modes of the bisphenolate ligands, in the solid-state. Attempts to grow crystals adequate for these studies were successful for compounds 1a-TiBn$_2$, 1b-TiBn$_2$, 1c-Ti(OiPr)$_2$, 2-TiBn$_2$, 1b-ZrBn$_2$, 1c-ZrBn$_2$, and 3-ZrBn$_2$. The titanium complexes were all found to be five-coordinate in the solid state, with a trigonal bipyramid geometry. The two phenolate rings twist away from each-other to give rise to C$_2$-symmetric structures. Analysis of the structures of 1a-TiBn$_2$ and 1b-TiBn$_2$ indicates that increasing the steric bulk forces the phenolate rings to twist further away from each other, but the distance between the substituents is not affected significantly. Comparison between 1a-TiBn$_2$ vs 2-TiBn$_2$ (FIG. 4) allows for the study of the effect of changing the linker while keeping the ortho substituents the same (t-Bu). Moving from pyridine to furan causes a small decrease in the twist angle (from 28° to about 24°). However, the distance between the ortho substituents increases substantially, by more than 2 Å from 9.11 Å to 11.29 Å. These structural trends indicate that the furan linker makes the metal center more sterically open by pulling the phenolate rings out. This may be the reason for the increased catalytic activity of 2-TiBn$_2$ vs 1a-TiBn$_2$. The zirconium complexes characterized in the solid-state present six-coordinate geometry with C$_s$-symmetric (1b-ZrBn$_2$ and 1c-ZrBn$_2$) and C$_1$-symmetric (3-ZrBn$_2$) binding modes of the ligand. Accommodation of an extra ligand in 1b-ZrBn$_2$ vs 1b-TiBn$_2$ suggests a more open and possibly more electrophilic center—reflected in the increased polymerization activity.

Example 4

Figure 13:
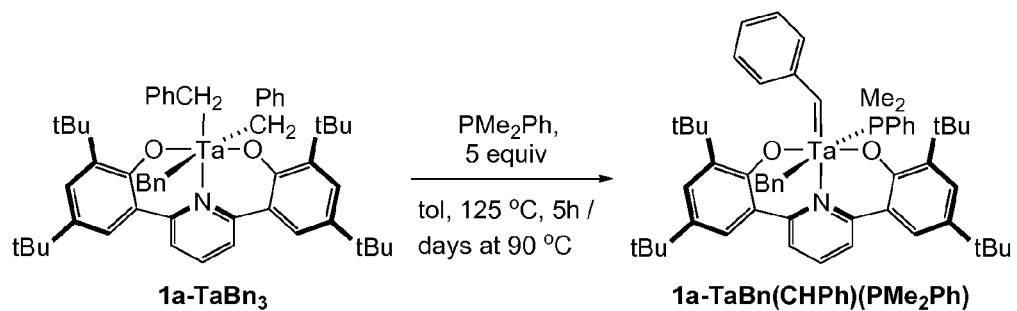
FIG. 13 shows a schematic illustration of an exemplary reaction scheme for the preparation of a tantalum benzylidene according to an embodiment herein described.
Figure 14:
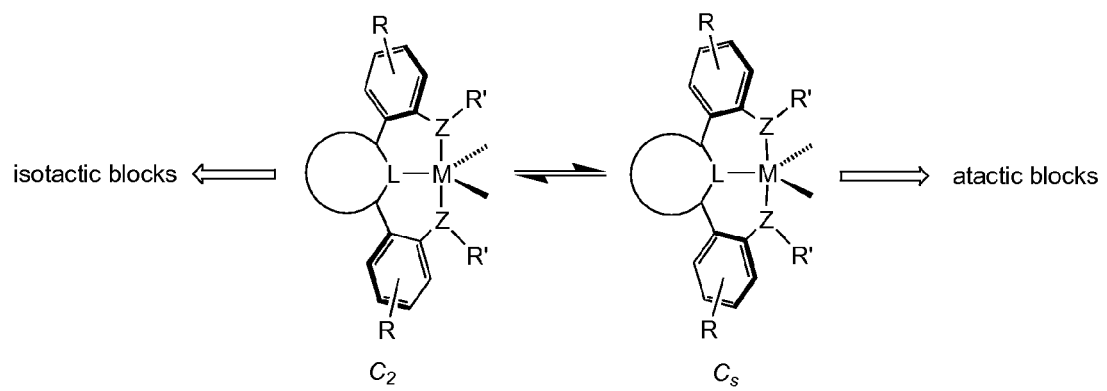
FIG. 14 is an illustration of equilibrium between geometries of organometallic complexes which can create stereoblock copolymers according to an exemplary embodiment herein described.

Preparation of Tantalum Benzylidene (FIG. 13)

Synthesis of 1a-TaBn$_3$ from TaCl$_2$(CH$_2$Ph)$_3$

KBn (78.5 mg, 0.604 mmol, 2 equiv) was added with the aid of C$_6$H$_6$ (4 mL) to a solution of 1a-H$_2$ (147 mg, 0.302 mmol, 1 equiv) in C$_6$H$_6$ (4 mL). This mixture was allowed to stir at room temperature for 1.5 h which afforded a colorless mixture of deprotonated phenol. A C$_6$H$_6$ solution of TaCl$_2$ (CH$_2$Ph)$_3$ (158.5 mg, 0.302 mmol, 1 equiv) was added and the reaction mixture was allowed to stir at room temperature for 10 h. Salts were removed by filtration through a bed of Celite and volatile materials were removed under vacuum. The resulting residue was suspended in petroleum ether and the mixture was cooled to −35° C. The desired product was collected by filtration and washed with cold petroleum ether. This procedure affords 168 mg (59% yield) of 1a-TaBn$_3$ as an orange powder.

Synthesis of 1a-TaBn$_3$ from Ta(CH$_2$Ph)$_5$

A C$_6$H$_6$ solution of 1a-H$_2$ (314.6 mg, 0.646 mmol, 1 equiv) was added to a Schlenk bomb charged with a solution of Ta(CH$_2$Ph)$_5$ (411 mg, 0.646 mmol, 1 equiv) in C$_6$H$_6$ (20 mL total volume). The flask was sealed, immersed in an oil bath at 60° C., and stirred for 5 h. Volatile materials were removed under vacuum and petroleum ether was added and the mixture was stored at −35° C. Compound 1a-TaBn$_3$ was collected by filtration and washed with cold petroleum ether (484 mg, 79% yield). $^1$H NMR (500 MHz, C$_6$D$_6$) δ: 1.35 (s, 18H, C(CH$_3$)$_3$), 1.78 (s, 18H, C(CH$_3$)$_3$), 3.08 (s, 4H, TaCH$_2$), 3.88 (s, 2H, TaCH$_2$), 6.25 (t, 2H, aryl-H), 6.36 (t, 4H, aryl-H), 6.45 (d, 4H, aryl-H), 6.69 (t, 1H, aryl-H), 7.04-7.06 (m, 3H, aryl-H overlap), 7.18 (d, 2H, aryl-H), 7.52 (t, 2H, aryl-H), 7.72 (t, 2H, aryl-H), 7.78 (t, 2H, aryl-H). $^{13}$C NMR (125 MHz, C$_6$D$_6$) δ: 31.1 (C(CH$_3$)$_3$), 32.1 (C(CH$_3$)$_3$), 35.0 (C(CH$_3$)$_3$), 36.0 (C(CH$_3$)$_3$), 73.5 (TaCH$_2$), 81.6 (TaCH$_2$), 122.9, 124.7, 125.2, 126.6, 127.2, 127.8, 128.0, 128.3, 129.2, 132.1, 138.1, 139.3, 143.1, 144.8, 152.3, 154.8, 156.9 (aryl). Anal. calcd. for C$_{54}$H$_{64}$NO$_2$Ta (%): C, 68.99; H, 6.86; N, 1.49. Found: C, 69.10; H, 7.38; N, 1.49.

Synthesis of 1a-TaBn (CHPh)(PMe$_2$Ph)

A toluene (5 mL) solution of 1a-TaBn$_3$ (115 mg, 0.122 mmol, 1 equiv) and PMe$_2$Ph (84.5 mg, 0.612 mmol, 5 equiv) was placed in a Schlenk flask fitted with a Screw in Teflon stopper. The flask was sealed and immersed in an oil bath at 125° C. Upon stirring for 5 hours, the mixture was allowed to cool to room temperature and volatile materials were removed under vacuum. Petroleum ether was added and desired product was recrystallized at −35° C. Collection by filtration affords 55.4 mg (46% yield) of 1a-TaBn(CHPh) (PMe$_2$Ph). $^1$H NMR (500 MHz, CD$_2$Cl$_2$) δ: 1.10 (br s, 6H, P(CH$_3$)$_2$), 1.41 (s, 18H, C(CH$_3$)$_3$), 1.60 (s, 18H, C(CH$_3$)$_3$), 2.20 (s, 2H, TaCH$_2$), 5.96 (d, 2H, aryl-H), 6.23 (t, 1H, aryl-H), 6.40 (t, 2H, aryl-H), 6.79 (t, 1H, aryl-H), 6.9-7.2 (br s and sharp d and t, 9H, aryl-H), 7.31 (t, 2H, aryl-H), 7.46 (d, 2H, aryl-H), 7.55 (d, 2H, aryl-H), 7.68 (t, 1H, aryl-H), 8.59 (s, 1H, TaCHPh). $^{13}$C NMR (125 MHz, CD$_2$Cl$_2$) δ: 13.8 (br P(CH$_3$)$_2$), 30.6 (C(CH$_3$)$_3$), 32.0 (C(CH$_3$)$_3$), 35.0 (C(CH$_3$)$_3$), 35.9 (C(CH$_3$)$_3$), 60.6 (br TaCH$_2$), 119.7, 124.3, 124.6, 126.3, 126.6, 126.9, 127.1, 128.0, 128.4, 128.5, 129.1 (br), 130.8, 130.9, 131.0, 137.7, 139.0, 143.6, 148.3, 153.1, 153.7, 158.7 (aryl), 243.0 (TaCHPh).

Example 5

Polymerization Procedures

Propylene Polymerization

An Andrews Glass Co. vessel is charged with MAO and toluene and fitted with a pressure regulator with a Swagelok quick-connect valve and septum. The vessel was sealed and attached to a propylene tank and purged. Upon cooling to 0° C., propylene (34-39 mL) was condensed. The catalyst is dissolved in toluene and injected into the vessel. The reaction mixture was stirred vigorously at 0° C. for the desired amount of time. After the polymerization is complete, the system is vented and the residue is quenched with acidified methanol. The polymers are filtered and dried under vacuum. Analysis of the polymers included $^1$H and $^{13}$C NMR (C$_2$D$_2$Cl$_4$) at elevated temperature (120-150° C.) with an acquisition time of 2 s and a delay of 6 s. Melting temperatures were obtained by DSC. Samples were sent to Dow (Midland, Mich.) for GPC analysis. If oligomers rather than polymers are formed, the MeOH/HCl solution is extracted with pentane (2×). t-Butyl-benzene (0.5 mL) was added to the combined organics and the mixture was analyzed by GC and GC-MS. The results obtained with exemplary titanium pre catalysts, zirconium precatalysts and vanadium pre catalysts are reported in the following Table 1, 2 and 3 respectively.

TABLE 1

Polymerization runs with titanium precatalysts and propylene.

| Run# | Precatalyst | Cat mmols | Time h | Solvent (3 + 0.7 mL) | Liquid C$_3$H$_6$ (mL, 0 C) | MAO (g) | MAO (equiv) | Polymer (mg) | Activity (g/mol · h) |
|---|---|---|---|---|---|---|---|---|---|
| 1 | 1a-TiBn$_2$ | 0.007 | 0.5 | PhMe | 34-39 mL | 0.207 | 500 | 3 | 8.6E+02 |
| 2 | 1a-TiBn$_2$ | 0.007 | 0.5 | PhMe | 34-39 mL | 0.207 | 500 | 2 | 5.7E+02 |
| 3 | 1a-TiBn$_2$ | 0.007 | 2.6 | PhMe | 34-39 mL | 0.207 | 500 | 14 | 7.7E+02 |
| 4 | 1a-TiBn$_2$ | 0.007 | 2 | PhMe | 34-39 mL | 0.207 | 500 | 8 | 5.7E+02 |
| 5 | 1a-TiBn$_2$ | 0.007 | 2 | PhMe | 34-39 mL | 0.207 | 500 | 7 | 5.0E+02 |
| 6 | 1a-TiBn$_2$ | 0.007 | 2 | PhCl | 34-39 mL | 0.207 | 500 | 17 | 1.2E+03 |
| 7 | 1a-TiBn$_2$ | 0.007 | 2 | PhCl | 34-39 mL | 0.207 | 500 | 20 | 1.4E+03 |
| 8 | 1b-TiBn$_2$ | 0.007 | 2 | PhMe | 34-39 mL | 0.207 | 500 | 35 | 2.5E+03 |
| 9 | 1b-TiBn$_2$ | 0.007 | 2 | PhMe | 34-39 mL | 0.207 | 500 | 32 | 2.3E+03 |
| 10 | 1b-TiBn$_2$ | 0.007 | 2 | PhCl | 34-39 mL | 0.207 | 500 | 30 | 2.1E+03 |
| 11 | 1b-TiBn$_2$ | 0.007 | 2 | PhCl | 34-39 mL | 0.207 | 500 | 30 | 2.1E+03 |
| 12 | 2-TiBn$_2$* | 0.007 | 0.5 | PhMe | 34-39 mL | 0.207 | 500 | 870 | 2.5E+05 |
| 13 | 2-TiBn$_2$* | 0.007 | 0.5 | PhMe | 34-39 mL | 0.207 | 500 | 1570 | 4.5E+05 |
| 14 | 3-TiBn$_2$* | 0.007 | 2 | PhMe | 34-39 mL | 0.207 | 500 | 1940 | 1.4E+05 |
| 15 | 3-TiBn$_2$* | 0.007 | 2 | PhMe | 34-39 mL | 0.207 | 500 | 2130 | 1.5E+05 |
| 16 | 1c-TiCl$_2$(THF) | 0.053 | 0.5 | PhMe | 34-39 mL | 0.310 | 1000 | 44 | 1.6E+04 |
| 17 | 1c-TiCl$_2$(THF) | 0.053 | 0.5 | PhMe | 34-39 mL | 1.500 | 500 | 834 | 3.1E+04 |
| 18 | 1c-TiBn$_2$ | 0.005 | 0.5 | PhMe | 34-39 mL | 0.290 | 1000 | 23 | 9.2E+03 |
| 19 | 1c-TiBn$_2$ | 0.025 | 0.5 | PhMe | 34-39 mL | 1.470 | 1000 | 63 | 5.0E+03 |

*Oligomers are obtained for these runs

TABLE 2

Polymerization runs with zirconium precatalysts and propylene.

| Run# | Precatalyst | Cat mmols | Time h | Solvent (3 + 0.7 mL) | Liquid C$_3$H$_6$ (mL, 0 C) | MAO (g) | MAO (equiv) | Polymer (mg) | Activity (g/mol · h) |
|---|---|---|---|---|---|---|---|---|---|
| 1 | 1a-ZrBn$_2$ | 0.007 | 0.5 | PhMe | 34-39 mL | 0.207 | 500 | 202 | 5.8E+04 |
| 2 | 1a-ZrBn$_2$ | 0.007 | 2 | PhMe | 34-39 mL | 0.207 | 500 | 702 | 5.0E+04 |
| 3 | 1a-ZrBn$_2$ | 0.007 | 2 | PhMe | 34-39 mL | 0.207 | 500 | 322 | 2.3E+04 |
| 4 | 1a-ZrBn$_2$ | 0.007 | 1.5 | PhMe | 34-39 mL | 0.414 | 1000 | 11120 | 1.1E+06 |
| 5 | 1a-ZrBn$_2$ | 0.0035 | 0.5 | PhMe | 34-39 mL | 0.207 | 1000 | 71 | 4.1E+04 |
| 6 | 1a-ZrBn$_2$ | 0.0035 | 0.5 | PhMe | 34-39 mL | 0.414 | 2000 | 904 | 5.2E+05 |
| 7 | 1a-ZrBn$_2$ | 0.0035 | 0.5 | PhMe | 34-39 mL | 0.621 | 3000 | 1717 | 9.8E+05 |
| 8 | 1a-ZrBn$_2$ | 0.0035 | 0.5 | PhMe | 34-39 mL | 0.828 | 4000 | 404 | 2.3E+05 |
| 9 | 1b-ZrBn$_2$ | 0.007 | 2 | PhMe | 34-39 mL | 0.207 | 500 | 9573 | 6.8E+05 |
| 10 | 1b-ZrBn$_2$ | 0.007 | 2 | PhMe | 34-39 mL | 0.207 | 500 | 7096 | 5.1E+05 |
| 11 | 1b-ZrBn$_2$ | 0.0035 | 0.5 | PhMe | 34-39 mL | 0.207 | 1000 | 2260 | 1.3E+06 |
| 12 | 1b-ZrBn$_2$ | 0.0035 | 0.5 | PhMe | 34-39 mL | 0.207 | 1000 | 1940 | 1.1E+06 |
| 13 | 1b-ZrBn$_2$ | 0.0035 | 0.5 | PhMe | 34-39 mL | 0.207 | 1000 | 2610 | 1.5E+06 |
| 14 | 2-ZrBn$_2$ | 0.0007 | 0.5 | PhMe | 34-39 mL | 0.207 | 5000 | 417 | 1.2E+06 |
| 15 | 2-ZrBn$_2$ | 0.0007 | 0.5 | PhMe | 34-39 mL | 0.207 | 5000 | 1621 | 4.6E+05 |
| 16 | 3-ZrBn$_2$ | 0.007 | 0.5 | PhMe | 34-39 mL | 0.414 | 1000 | 3260 | 9.3E+05 |
| 17 | 3-ZrBn$_2$ | 0.007 | 0.5 | PhMe | 34-39 mL | 0.207 | 500 | 5620 | 1.6E+06 |
| 18 | 1c-ZrBn$_2$ | 0.0024 | 0.5 | PhMe | 34-39 mL | 0.140 | 1000 | 34 | 2.8E+04 |
| 19 | 1c-ZrBn$_2$ | 0.0024 | 0.5 | PhMe | 34-39 mL | 0.696 | 5000 | 502 | 5.0E+05 |

TABLE 3

Polymerization runs with vanadium precatalysts and propylene e.

| Run# | Precatalyst | Cat mmols | Time h | Solvent (3 + 0.7 mL) | Liquid $C_3H_6$ (mL, 0 C) | MAO (g) | MAO (equiv) | Polymer (mg) | Activity (g/mol · h) |
|---|---|---|---|---|---|---|---|---|---|
| 1 | 1c-VCl(THF)$_2$ | 0.005 | 0.5 | PhMe | 34-39 mL | 0.147 | 500 | 313 | 1.2E+05 |
| 2 | 1c-VCl(THF)$_2$ | 0.005 | 0.5 | PhMe | 34-39 mL | 0.294 | 1000 | 478 | 1.9E+05 |
| 3 | 1c-VCl(THF)$_2$ | 0.005 | 0.5 | PhMe | 34-39 mL | 0.589 | 2000 | 894 | 3.5E+05 |
| 4 | 1c-VCl(THF)$_2$ | 0.005 | 0.5 | PhMe | 34-39 mL | 0.887 | 3000 | 2038 | 8.0E+05 |
| 5 | 1c-VCl(THF)$_2$ | 0.005 | 0.5 | PhMe | 34-39 mL | 1.180 | 4000 | 1606 | 6.3E+05 |

1-Hexene and 1-Octene Polymerization

A specially made 15 mL Schlenk flask that fits a septum on the side arm is charged with MAO and tetradecane (internal standard). Toluene and monomer are vacuum transferred into the reaction vessel in the desired amount. While purging with argon, an aliquot is removed and quenched with butanol for the initial GC trace. The catalyst is dissolved in toluene and injected into the vessels. At intervals during the polymerization, aliquots are removed and quenched for GC analysis. When the polymerization has proceeded to the desired completion, the vessel is vented and the residue is quenched with acidified methanol. The polymers are filtered and dried under vacuum and analyzed in the same fashion as polypropylene. The results obtained with exemplary titanium precatalysts are reported in Table 4.

TABLE 4

Polymerization runs with titanium precatalysts and 1-hexene in toluene.

| Run # | Precatalyst | Cat Mmols | Time h | [$C_6H_{12}$] in toluene | MAO (g) | MAO (equiv) | Polymer (mg) | Activity (g/mol · h) |
|---|---|---|---|---|---|---|---|---|
| 1 | 1c-TiCl$_2$(THF) | 0.005 | 6 | 1.98 | 0.147 | 500 | 352 | 1.1E+03 |
| 2 | 1c-TiCl$_2$(THF) | 0.005 | 2 | 5.63 | 0.145 | 500 | 266 | 2.5E+03 |
| 3 | 1c-TiCl$_2$(THF) | 0.005 | 2 | 5.84 | 0.145 | 500 | 136 | 1.3E+03 |
| 4 | 1c-TiCl$_2$(THF) | 0.005 | 0.5 | 6.15 | 0.145 | 500 | 63 | 2.4E+03 |
| 5 | 1c-TiCl$_2$(THF) | 0.005 | 0.5 | neat | 0.145 | 500 | 286 | 1.1E+04 |
| 6 | 1c-TiCl$_2$(THF) | 0.005 | 0.5 | neat | 0.145 | 500 | 502 | 1.9E+04 |
| 7 | 1c-TiCl$_2$(THF) | 0.005 | 1.5 | 2.50 | 0.290 | 1000 | 291 | 3.7E+03 |
| 8 | 1c-TiCl$_2$(THF) | 0.005 | 3 | 2.70 | 0.290 | 1000 | 384 | 2.4E+03 |
| 9 | 1c-TiCl$_2$(THF) | 0.005 | 1.5 | 6.84 | 0.290 | 1000 | 522 | 6.6E+03 |
| 10 | 1c-TiCl$_2$(THF) | 0.005 | 2.2 | 8.00 | 0.290 | 1000 | 384 | 3.2E+03 |
| 11 | 1c-TiCl$_2$(THF) | 0.005 | 0.75 | neat | 0.290 | 1000 | 1004 | 2.5E+04 |

Ethylene/1-Octene Co-polymerization

A specially made 15 mL Schlenk flask that fits a septum on the side arm is charged with MAO (290 mg, 1000 eq), 1-octene (2 mL), and toluene (10 mL). The vessel is degassed and then subjected to one atmosphere of ethylene. The catalyst (5 μmol) is dissolved in toluene and injected into the vessel. After 1.5 hours, the vessel is vented and the residue is quenched with acidified methanol. The polymers are filtered and dried under vacuum and analyzed in the same fashion as polypropylene. Results obtained are reported in Table 5.

TABLE 5

The results of the ethylene/1-octene copolymerization.

| Run # | Precatalyst | Polymer (mg) | Activity (g/mol · h) | Comonomer incorporation (%) |
|---|---|---|---|---|
| 1 | 1c-TiCl$_2$(THF) | 20 | 2.7E+03 | n/a |
| 2 | 1c-ZrBn$_2$ | 1200 | 1.6E+05 | 0.5 |
| 3 | 1c-VCl (THF)$_2$ | 374 | 4.9E+04 | 6.3 |

Propylene Polymerization and Oligomerization with Titanium Complexes

The propylene polymerization reactivity of the present titanium species, upon activation with excess MAO has been investigated. Titanium pyridine bisphenolate systems were found to be about three orders of magnitude less active than the zirconium counterparts. One polymer sample, obtained in quantities sufficient for analysis indicated that the obtained polymers are high molecular weight and show no olefin signals in the $^{13}$C NMR spectra. The methyl region of the $^{13}$C NMR spectrum shows a significant peak corresponding to the mmmm pentad overlapping with a distribution of peaks corresponding to atactic polymer. The nature of the solvent (toluene vs chlorobenzene) was found not to influence activity significantly. The observed lower activity compared to zirconium could be attributed to a more crowded environment around the titanium center. Analysis of the precursors may hint to the features that control reactivity in these systems. Comparing the solid-state structures of the 1b-ZrBn$_2$ and 1b-TiBn$_2$ shows that the zirconium center accommodates a sixth ligand in its coordination sphere, unlike titanium. A more open metal center could possibly be more active for insertion but also for β-H elimination, which are observed for zirconium. Furthermore the zirconium precursor is $C_s$-symmetric while the titanium one is $C_2$-symmetric. The symmetry of the titanium system may have contributed to the observed fraction containing isotactic enrichment. It is important to note that while the precursors are well defined, the active cationic species are not, and may have geometries different from the ones observed in the precursors.

Titanium complexes supported by the furan (2-TiBn$_2$) and thiophene (3-TiBn$_2$) linked frameworks show high activity for the oligomerization of propylene. The oligomer products separate as oils upon quenching with HCl/MeOH and have been analyzed by GC, GC-MS, and NMR spectroscopy. The furan system was found to generate mainly $C_9$ to $C_{21}$ oligomers, while the thiophene one generates a broader distribution of oligomers —$C_9$ to $C_{33}$. $^{13}$C NMR spectra of the resulting oligomer mixtures show many olefin peaks along with a complicated aliphatic region. The complex spectra may be due to titanium chain-walking or to isomerization by acid catalysis during workup. Clearly, β-H elimination is a facile process in these systems. The increased activity of 2-TiBn$_2$ and 3-TiBn$_2$ compared to the pyridine based systems may be due to a more open metal center. This is apparent in the solid-state structures of 2-TiBn$_2$ and 1a-TiBn$_2$. Compared to the pyridine system (1a-TiBn$_2$), the furan based system (2-TiBn$_2$) shows a significant increase in the distance between the bulky ortho-t-butyl groups from 9.1 to 11.3 Å. This "opening" of the metal center could lead to faster insertion rates as well as the increased propensity for β-H elimination, both phenomena being observed.

Propylene Polymerization and Oligomerization with Zirconium Complexes

Propylene polymerization trials have been performed with the present complexes at 0° C., upon activation with excess methylaluminumoxane (MAO). The zirconium species generate polymers which are separated from the quenched methanol/hydrochloric acid mixture by decantation or filtration. These materials are rinsed with water and placed under vacuum at 80° C. to remove volatile materials, then weighed and analyzed by various techniques including $^1$H and $^{13}$C NMR spectroscopy, GPC, and GC-MS. The MAO activated zirconium complexes have been found to be very active polymerization catalysts. In some cases, the activity exceeds 106 g polypropylene/(mol Zr·h) which is comparable with activities observed for some of the most active propylene polymerization catalysts known.

Figure 7:
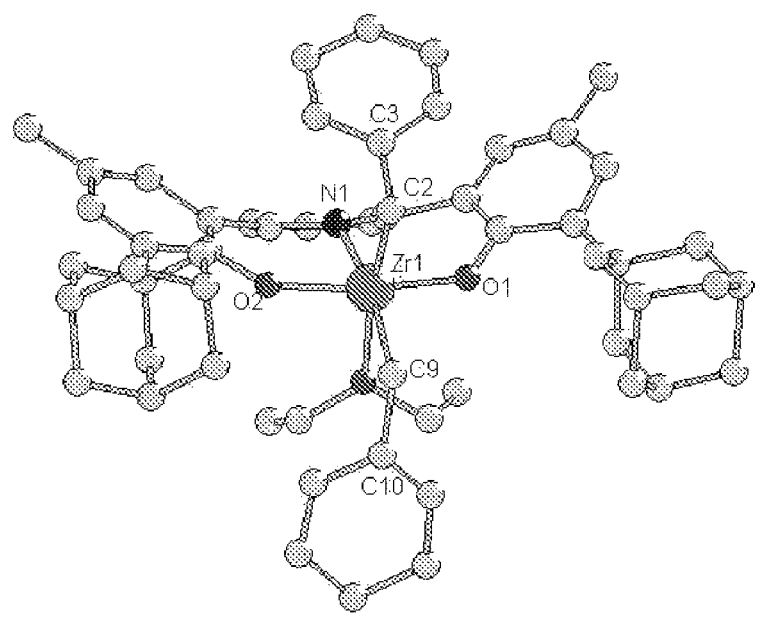
FIG. 7 shows a schematic illustration of the structure of an exemplary organometallic complex according to an embodiment herein described, wherein the hydrogen atoms have been omitted for clarity.
Figure 8A:
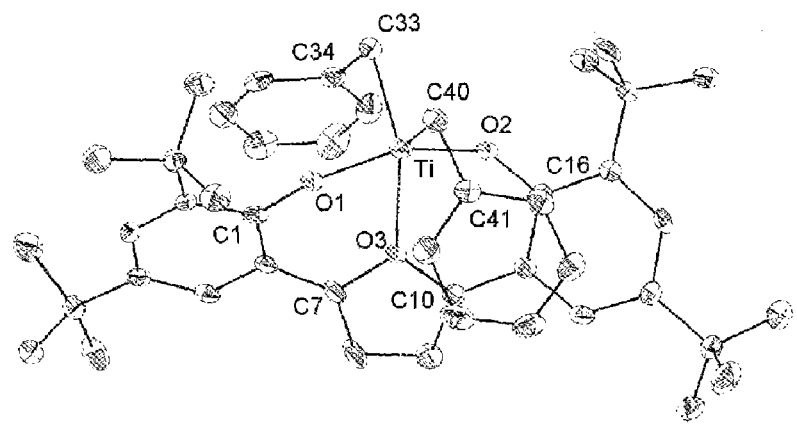
FIGS. 8A and 8B shows a schematic illustration of the structure of an exemplary organic metallic complex according to an embodiment herein described. View A is roughly perpendicular to the Ti—O vector and view B is along the Ti—O vector.
Figure 8B:
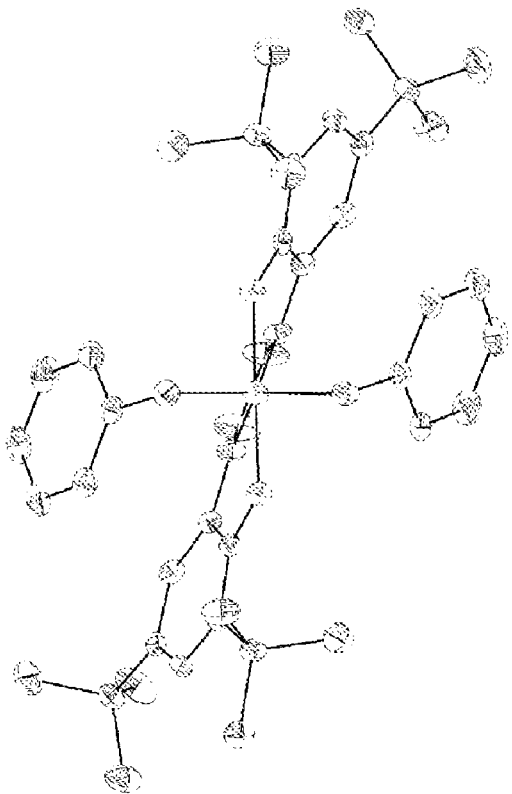

Polymers obtained from the zirconium pyridine-bisphenolate systems (1a-ZrBn$_2$ and 1b-ZrBn$_2$) were investigated by GPC. Interestingly, the polymer molecular weight distribution was found to be bimodal, with both fractions displaying low PDIs (FIG. 7). For polymers obtained from 1a-ZrBn$_2$, the high molecular weight fractions ($M_W$=1.6·10$^5$–1.9·10$^5$) were found to have PDIs between 1.9 and 2.5 while the low molecular weight ones are around 1.5 ($M_W$=1.3·10$^5$). An MAO dependence of the molecular weight distribution was observed. On varying the MAO excess from 2000 to 4000 equivalents, the molecular weight distribution shifts toward the low molecular weight polymers. $^{13}$C NMR analysis of the resulting polymers shows significant peaks corresponding to i-butyl terminal groups, peaks that increased in propensity with increasing MAO excess. (Lin, S.; Waymouth, R. M. *Macromolecules* 1999, 32, 8283-8290. Cheng, H. N.; Smith, D. A. *Macromolecules* 1986, 19, 2065-2072.) The polymerization activity was found to be dependent on MAO excess, with maximum activities at intermediate MAO excess. Polymers generated from 1b-ZrBn$_2$ or from 1a-ZrBn$_2$ with low 500 equiv MAO have few i-butyl end-groups ($^{13}$C NMR spectroscopy), but display terminal and internal olefin peaks as well as n-propyl end-groups. GC-MS analysis revealed that polymers from 1b-ZrBn$_2$ display some low molecular weight oligomers of propylene (<$C_{30}$).

The small PDIs observed for each polymer fraction indicates that single-site catalysts are involved. The observed bimodal distribution is probably due to the presence of two types of catalysts, the relative distribution of which is dependent of the amount of MAO utilized. The presence of i-butyl terminal groups is indicative of chain transfer to aluminum. If 1,2-insertion is the propagation regiochemistry, then i-butyl terminal groups could form at both ends of the polymer, by insertion into the initial Zr-Me bond as well as by chain transfer of a CH$_2$CH(Me)(Polymeryl) group from zirconium to aluminum followed by quenching with acid. The increase in i-butyl end-groups with increasing the excess of MAO is consistent with an increased amount of chain transfer to aluminum. The diverse set of olefin resonances observed in some of the samples may be indicative of metal chain-walking or possibly of acid catalyzed isomerization upon work-up. Samples that show olefin signals ($^{13}$C NMR spectroscopy) were also found to show a similar amount of n-propyl end groups, consistent with termination events based on β-H elimination and with 1,2-insertion of propylene into the generated metal hydride. The observed predominant end-groups are consistent with a preference for 1,2-insertion of propylene into both Zr—H and Zr—C bonds. The differences in behavior between 1a-ZrBn$_2$ and 1b-ZrBn$_2$, with regard to the presence of oligomers, i-butyl end-groups, effect of excess MAO, and propensity for β-H elimination could be attributed to a variety of factors. For example, the bulkier system 1b-ZrBn$_2$ may hinder chain transfer to aluminum and hence decrease the number of i-butyl end groups.

To investigate the ability of the zirconium pyridine-bisphenolate systems to support polymerization catalysis upon stoichiometric activation, the reaction of 1b-ZrBn$_2$ with [Ph$_3$C][B(C$_6$F$_5$)$_4$] was performed in C$_6$D$_5$Cl, in a J-Young tube. This reaction is not clean, but formation of one major species was observed by $^1$H NMR spectroscopy. Excess 1-hexene was added to the mixture and allowed to react for three hours. $^1$H NMR spectroscopy shows almost complete disappearance of the 1-hexene peaks and appearance of new signals in the olefin region. After allowing to stand at room temperature for a day, another portion of 1-hexene was added and consumption of the monomer was observed again (the second time to a lower extend than the first). These observations indicate that the cationic zirconium species resulting from stoichiometric activation of 1b-ZrBn$_2$ is active for the oligomerization of 1-hexene. While chain termination (or transfer) occurs frequently, the resulting zirconium species remain active for oligomerization for extended periods of time and even after the monomer is essentially consumed.

Complexes 2-ZrBn$_2$ and 3-ZrBn$_2$ show high polymerization activity as well upon activation with MAO. Complex 3-ZrBn$_2$ leads to atactic polymers with a small amount of olefin and n-propyl end groups ($^{13}$C NMR spectrum). GC analysis shows the absence of low propylene oligomers. This is in contrast with the outcome of the polymerization trials with 3-ZrBn$_2$ which leads to abundant formation of oily oligomers along with some higher polymers. A statistical distribution of C$_9$ to C$_{45}$ oligomers was observed by GC and GC-MS analysis in this case. $^{13}$C NMR spectra of these samples show olefin peaks and n-propyl terminal groups. These results, while not well understood, show that changing the nature of the linker leads to differences in the outcome of propylene polymerizations.

Propylene Polymerizations with Vanadium Complexes

Polymerizations have been performed with 1c-VCl(THF)$_2$ upon activation with MAO. The effects of amount of activator and propylene concentration on activity, tacticity, and molecular weight have been studied. The number of equivalents of MAO has a distinct effect on the activity such that maximum activity is reached with 3000 equivalents. The activities achieved with this catalyst are higher than for either the titanium or the zirconium species with the same ligand (1c-H$_2$). These polymers are very insoluble which, is a likely result of very high molecular weight. The PDI of approximately two indicates that there is only one active catalytic species.

1-Hexene Polymerizations with Titanium Complexes

A stock solution of 1c-TiCl$_2$(THF) in toluene was prepared and injected into a flask containing MAO, 1-hexene and, in some cases, toluene. The polymerizations were monitored by GC for 1-hexene conversion, and the generated polymer was isolated and analyzed. In general, activity increases with increasing 1-hexene concentration, a result of the increased amount of monomer available for polymerization. However, increasing 1-hexene concentration decreases conversion such that a plot of 1-hexene conversion versus time approaches an asymptote. The $^{13}$C NMR spectra of these polymers show that they are atactic.

Ethylene/1-Octene Copolymerizations

A series of ethylene/1-octene copolymerizations were run for precatalysts bearing the 1c ligand. Solutions of these precatalysts in toluene were prepared and injected into flasks containing MAO, 1-octene, toluene, and one atmosphere of ethylene. The generated polymer was isolated and analyzed. In general, very little 1-octene incorporation was observed.

It is to be understood that the disclosures are not limited to particular compositions or catalyst systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the disclosure pertains. Although any methods and materials similar or equivalent to those described herein can be used in the practice for testing of the disclosure(s), specific examples of appropriate materials and methods are described herein.

In the molecular structures herein, the use of bold and dashed lines to denote particular conformation of groups follows the IUPAC convention. A bond indicated by a broken line indicates that the group in question is below the general plane of the molecule as drown, and a bond indicated by a bold line indicates that the group at the position in question is above the general plane of the molecule as drown.

The examples set forth above are provided to give those of ordinary skill in the art a complete and description of how to make and use the embodiments of the organometallic complexes, methods and systems herein disclosed, and are not intended to limit the scope of what the applicants regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this application are incorporated by reference to the same extent as if each reference had been incorporated by reference in its entirety individually.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A non-metallocene organometallic complex comprising a tridentate ligand, wherein the tridentate ligand is a dianionic or trianionic ligand having the structure of formula

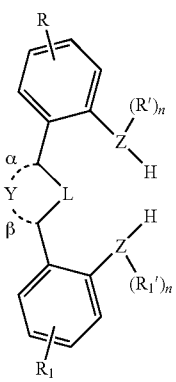

(I)

wherein
L is an atom that when contacted with a metal can donate one or more of its electrons through a coordinate covalent bond to, or shares its electrons through a covalent bond with the metal
Z is a group 14, a group 15 or group 16 anionic donor,
Y is a an organic fragment selected from the group consisting of a hydrocarbylene, substituted hydrocarbylene, heteroatom-containing hydrocarbylene or substituted heteroatom-containing hydrocarbylene linker, wherein Y and L are linked together to form a cyclic group;
R, R$_1$ R' and R'$_1$ are independently selected from hydrogen, hydrocarbyl, substituted hydrocarbyl, heteroatom containing hydrocarbyl, or other functional group,
α and β are independently single or multiple bonds; and n is 0, 1 or 2
wherein the metal, R, R$_1$, and the cyclic group are selected to provide the resulting non-metallocene organometallic complex with a Cs geometry, a C$_1$ geometry, a C$_2$ geometry or a C$_{2v}$ geometry.

2. The non-metallocene organometallic complex of claim 1, having the structure of formula (II)

$$\text{(II)}$$

wherein
M is a metal, q is the metal coordination number and is 4, 5, 6, or 7, p is the metal oxidation state and is any state from 0 to +6, and x is 2 or 3;
L' is a neutral coordinating group, displaying a group 15 or 16 atom donor,
Z is a group 14, a group 15 or group 16 anionic donor,
L is an atom that can donate one or more of its electrons through a coordinate covalent bond to, or shares its electrons through a covalent bond with the metal
Y is an organic fragment, selected from the group consisting of a hydrocarbylene, substituted hydrocarbylene, heteroatom-containing hydrocarbylene or substituted heteroatom-containing hydrocarbylene linker, wherein Y and L are linked together to form a cyclic group,
α, β and γ are independently single or multiple bonds;
R, $R_1$, R' $R'_1$ and R" are independently selected from hydrogen, hydrocarbyl, substituted hydrocarbyl, heteroatom containing hydrocarbyl, and functional groups, and might be the same or different;
n is 0, 1 or 2,
t is 0, 1, 2 or 3,
t=q−3−(p−x) and
q≧p.

3. The non-metallocene organometallic complex of claim 2, wherein M is a metal selected from the group consisting of group III metals, group IV metals, group V metals, lanthanide metals, and actinide metals.

4. The non-metallocene organometallic complex of claim 2, wherein Z is selected from the group consisting of a O, S, Se, Te, N, P, As, and Sb.

5. The non-metallocene organometallic complex of claim 2, wherein Z is N or O.

6. The non-metallocene organometallic complex of claim 2, wherein the cyclic group is a substituted or unsubstituted pyridine, thiophene, furan or benzene.

7. The non-metallocene organometallic complex of claim 2, wherein R and are $R_1$ are independently selected from the group consisting of alkyl, aryl, silyl, boryl, and halide.

8. The non-metallocene organometallic complex of claim 2, wherein R' and $R'_1$ are independently selected from the group consisting of alkyl, aryl, and silyl.

9. The non-metallocene organometallic complex of claim 2, wherein R" is a selected from the group consisting of halide alkyl, aryl, hydride, triflate, carboxilate, amide, alkoxide and a combination thereof.

10. A method for preparing polyolefins, the method comprising contacting an olefin with the non-metallocene organometallic complex of claim 1.

11. The method of claim 10, wherein contacting an olefin with the non-metallocene organometallic complex is performed in a reaction mixture further comprising a suitable activator.

12. The method of claim 11, wherein the non-metallocene organometallic complex is a non-metallocene organometallic complex of formula (II) wherein x is 2.

13. The method of claim 10, wherein the non-metallocene organometallic complex has a $C_2$ geometry and the olefin polymer is an isotactic olefin polymer.

14. The method of claim 10, wherein the non-metallocene organometallic complex has a $C_s$ geometry and the olefin polymer is an atactic olefin polymer.

15. The method of claim 10, wherein the non-metallocene organometallic complex has a $C_{2v}$ geometry and the olefin polymer is an atactic olefin polymer.

16. The method of claim 10, wherein the non-metallocene organometallic complex has a $C_1$ geometry, and the olefin polymer is an isotactic and/or atactic olefin polymer.

17. The method of claim 10, wherein the non-metallocene organometallic complex has a $C_1$ geometry, the non-metallocene organometallic complex is unsymmetrical, and the olefin polymer is a syndiotactic olefin polymer.

18. The method of claim 10, wherein the non-metallocene organometallic complex is an non-metallocene organometallic complex of formula (II), wherein M is Titanium and L and Y are linked together to form a 5-membered cyclic group, whereby the polyolefin is a polymer having a low molecular weight.

19. The method of claim 10, wherein the non-metallocene organometallic complex is a non-metallocene organometallic complex of formula (II), wherein M is titanium or Vanadium, L and Y are linked together to form a 6-membered cyclic group, whereby the polyolefin is a polymer having a high molecular weight.

20. The method of claim 10, wherein the non-metallocene organometallic complex comprises an alkylidene and the olefin polymerization is a olefin polymerization metathesis reaction.

21. A catalytic system for olefin polymerization, the system comprising the non-metallocene organometallic complex of claim 1 and a suitable activator.

22. The catalytic system of claim 21, wherein the suitable activator is methylaluminoxane modified methylaluminoxane, trityl borate, a fluorinated borane, anilinium borate or a chain transfer agents.

23. A method for preparing polyolefins, the method comprising
contacting an olefin with a non-metallocene organometallic complex comprising
a tridentate ligand;
a metal bonded to the tridentate ligand,
the tridentate ligand comprising a first substituted aryl group, a second substituted aryl group and a cyclic group, each of the first and second substituted aryl groups substituted with at least an anionic donor, each of the first and second substituted aryl group connected to the cyclic group via semi-rigid ring-ring linkages at the ortho position with respect to the anionic donor, wherein the metal, the first substituted aryl group, the second substituted aryl group, and the cyclic group are selected to provide the resulting non-metallocene organometallic complex with a Cs geometry, a $C_1$ geometry, a $C_2$ geometry or a $C_{2v}$ geometry, wherein the non-metallocene organometallic complex has a $C_2$ geometry and the olefin polymer is an isotactic olefin polymer.

24. A method for preparing polyolefins, the method comprising contacting an olefin with the non-metallocene organometallic complex comprising a tridentate ligand;

a metal bonded to the tridentate ligand, the tridentate ligand comprising a first substituted aryl group, a second substituted aryl group and a cyclic group, each of the first and second substituted aryl groups substituted with at least an anionic donor, each of the first and second substituted aryl group connected to the cyclic group via semi-rigid ring-ring linkages at the ortho position with respect to the anionic donor, wherein the metal, the first substituted aryl group, the second substituted aryl group, and the cyclic group are selected to provide the resulting non-metallocene organometallic complex with a Cs geometry, a $C_1$ geometry, a $C_2$ geometry or a $C_{2v}$ geometry, wherein the non-metallocene organometallic complex has a $C_s$ geometry and the olefin polymer is an atactic olefin polymer.

25. A method for preparing polyolefins, the method comprising contacting an olefin with the non-metallocene organometallic complex comprising a tridentate ligand;

a metal bonded to the tridentate ligand, the tridentate ligand comprising a first substituted aryl group, a second substituted aryl group and a cyclic group, each of the first and second substituted aryl groups substituted with at least an anionic donor, each of the first and second substituted aryl group connected to the cyclic group via semi-rigid ring-ring linkages at the ortho position with respect to the anionic donor, wherein the metal, the first substituted aryl group, the second substituted aryl group, and the cyclic group are selected to provide the resulting non-metallocene organometallic complex with a Cs geometry, a $C_1$ geometry, a $C_2$ geometry or a $C_{2v}$ geometry, wherein the non-metallocene organometallic complex has a $C_{2v}$ geometry and the olefin polymer is an atactic olefin polymer.

26. A non-metallocene organometallic complex comprising a tridentate ligand; wherein the tridentate ligand is a dianionic or trianionic ligand having the structure of formula (II)

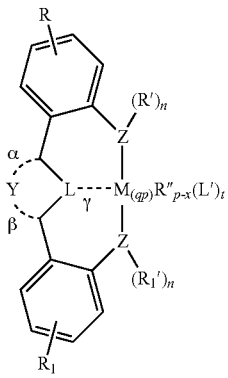

(II)

wherein

M is a metal, q is the metal coordination number and is 4, 5, 6, or 7, p is the metal oxidation state and is any state from 0 to +6, and x is 2 or 3;

L' is a neutral coordinating group, displaying a group 15 or 16 atom donor,

Z is a group 14, a group 15 or group 16 anionic donor,

L is an atom that can donate one or more of its electrons through a coordinate covalent bond to, or shares its electrons through a covalent bond with the metal Y is an organic fragment, selected from the group consisting of a hydrocarbylene, substituted hydrocarbylene, heteroatom-containing hydrocarbylene or substituted heteroatom-containing hydrocarbylene linker, wherein Y and L are linked together to form a cyclic group, α, β and γ are independently single or multiple bonds;

R, $R_1$, R' $R'_1$ and R" are independently selected from hydrogen, hydrocarbyl, substituted hydrocarbyl, heteroatom containing hydrocarbyl, and functional groups, and might be the same or different;

n is 0, 1 or 2, t is 0, 1, 2 or 3, t=q−3−(p−x) and q≧p, wherein the metal, R, $R_1$, and the cyclic group are selected to provide the resulting non-metallocene organometallic complex with a Cs geometry, a $C_1$ geometry, a $C_2$ geometry or a $C_{2v}$ geometry.

27. The non-metallocene organometallic complex of claim 26, wherein M is a metal selected from the group consisting of group III metals, group IV metals, group V metals, lanthanide metals, and actinide metals.

28. The non-metallocene organometallic complex of claim 26, wherein Z is selected from the group consisting of a O, S, Se, Te, N, P, As, and Sb.

29. The non-metallocene organometallic complex of claim 26, wherein Z is N or O.

30. The non-metallocene organometallic complex of claim 2, wherein the cyclic group is a substituted or unsubstituted pyridine, thiophene, furan or benzene.

* * * * *